US012239701B2

United States Patent
Kim et al.

(10) Patent No.: US 12,239,701 B2
(45) Date of Patent: Mar. 4, 2025

(54) RESPIRATORY SYNCYTIAL VIRUS MRNA VACCINE

(71) Applicant: Vernagen, LLC, Tucker, GA (US)

(72) Inventors: Baek Kim, Atlanta, GA (US); Jack Yoon, Suwanee, GA (US); David Pak, Suwanee, GA (US)

(73) Assignee: Vernagen, LLC, Tucker, GA (US)

( * ) Notice: Subject to any disclaimer, the term of this patent is extended or adjusted under 35 U.S.C. 154(b) by 105 days.

(21) Appl. No.: 18/394,486

(22) Filed: Dec. 22, 2023

(65) Prior Publication Data

US 2024/0261387 A1  Aug. 8, 2024

Related U.S. Application Data

(60) Provisional application No. 63/483,099, filed on Feb. 3, 2023.

(51) Int. Cl.
*A61K 39/155* (2006.01)
*A61K 39/00* (2006.01)
(Continued)

(52) U.S. Cl.
CPC .......... *A61K 39/155* (2013.01); *A61K 39/295* (2013.01); *A61P 37/04* (2018.01); *A61K 2039/53* (2013.01); *A61K 2039/70* (2013.01); *C12N 2760/18322* (2013.01); *C12N 2760/18334* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| 2018/0271970 A1 | 9/2018 | Ciaramella et al. |
| 2021/0170017 A1 | 6/2021 | Lutz et al. |
| 2022/0125909 A1 | 4/2022 | Moore et al. |

FOREIGN PATENT DOCUMENTS

WO  2021/249009 A1  12/2021

OTHER PUBLICATIONS

SEQ 1 with geneseq db access BGW72552 by Lutz et al. 2019.*
(Continued)

*Primary Examiner* — Shanon A. Foley
(74) *Attorney, Agent, or Firm* — Sughrue Mion, PLLC

(57) ABSTRACT

Provided herein are a respiratory syncytial virus (RSV) vaccine composition including a messenger ribonucleic acid (mRNA) including an open reading frame (ORF) encoding RSV mutant F B strain protein, and optionally a mRNA including an ORF encoding RSV mutant F A strain protein, and a method of inducing immune response against RSV by administering an effective amount of the RSV vaccine composition to a subject in need thereof. Provided herein are also a respiratory syncytial virus (RSV) and human metapneumovirus virus (hMPV) vaccine composition including a mRNA including an ORF encoding RSV mutant F A strain protein, a mRNA including an ORF encoding RSV mutant F B strain protein, and a mRNA including an ORF encoding hMPV F protein, and a method of inducing immune response against RSV and hMPV by administering an effective amount of the RSV and hMPV vaccine composition to a subject in need thereof.

27 Claims, 8 Drawing Sheets

Specification includes a Sequence Listing.

(51) Int. Cl.
*A61K 39/295* (2006.01)
*A61P 37/04* (2006.01)

(56) References Cited

OTHER PUBLICATIONS

International Search Report and Written Opinion of the International Searching Authority dated Mar. 6, 2024 for PCT/US2023/085663.

* cited by examiner

RESPIRATORY SYNCYTIAL VIRUS MRNA VACCINE

CROSS REFERENCE TO RELATED APPLICATIONS

This application claims priority to U.S. Provisional Application No. 63/483,099 filed Feb. 3, 2023, the entire disclosure of which is incorporated herein by reference.

INCORPORATION BY REFERENCE OF SEQUENCE LISTING

The content of the electronically submitted sequence listing, file name: A294002_substitute sequence listing as filed; size: 37,950 bytes; and date of creation: May 14, 2024, filed herewith, is incorporated herein by reference in its entirety.

FIELD

Provided herein are a respiratory syncytial virus (RSV) vaccine composition including a messenger ribonucleic acid (mRNA) including an open reading frame (ORF) encoding RSV mutant F B strain protein, and optionally a mRNA including an ORF encoding RSV mutant F A strain protein, and a method of inducing immune response against RSV by administering an effective amount of the RSV vaccine composition to a subject in need thereof.

Provided herein are also a respiratory syncytial virus (RSV) and human metapneumovirus virus (hMPV) vaccine composition including a mRNA including an ORF encoding RSV mutant F A strain protein, a mRNA including an ORF encoding RSV mutant F B strain protein, and a mRNA including an ORF encoding hMPV F protein, and a method of inducing immune response against RSV and hMPV by administering an effective amount of the RSV and hMPV vaccine composition to a subject in need thereof.

BACKGROUND

Respiratory syncytial virus (RSV) is a common respiratory virus that infects the nose, throat, lungs, and breathing passages. At present, there is no approved RSV vaccine, although the development of a vaccine would be one of the best strategies for preventing RSV. There has been a need for RSV vaccine.

Human metapneumovirus (hMPV) is a similar but separate virus. The seasonal epidemiology of hMPV is similar to that of RSV. At present, there is no approved RSV and hMPV vaccine, although the development of a vaccine would be one of the best strategies for preventing RSV and hMPV. There has been a need for RSV and hMPV vaccine.

SUMMARY

The present disclosure provides a respiratory syncytial virus (RSV) vaccine composition comprising a messenger ribonucleic acid (mRNA) comprising an open reading frame (ORF) encoding RSV mutant F B strain protein having an amino acid sequence of SEQ ID NO: 1. In one embodiment, the ORF encoding RSV mutant F B strain protein has a nucleotide sequence of SEQ ID NO: 2. In one embodiment, the mRNA comprising the ORF encoding RSV mutant F B strain protein further comprises a 5' untranslated region (UTR), a 3' UTR, and a poly (A) tail so as to have the structure of 5'UTR-ORF encoding RSV mutant F B strain protein-3'UTR-poly (A) tail, and the ORF encoding RSV mutant F B strain protein has a nucleotide sequence of SEQ ID NO: 2. In one embodiment, the poly (A) tail has a length of 50-250 nucleotides. In one embodiment, the mRNA having the structure of 5'UTR-ORF encoding RSV mutant F B strain protein-3'UTR-poly (A) tail has a nucleotide sequence of SEQ ID NO: 3. In another embodiment, the mRNA having the structure of 5'UTR-ORF encoding RSV mutant F B strain protein-3'UTR-poly (A) tail has a nucleotide sequence having at least 80% identity to SEQ ID NO: 3.

The present disclosure also provides a RSV vaccine composition comprising a mRNA comprising an ORF encoding RSV mutant F B strain protein having an amino acid sequence of SEQ ID NO: 1, and a mRNA comprising an ORF encoding RSV mutant F A strain protein having an amino acid sequence of SEQ ID NO: 5. In one embodiment, the ORF encoding RSV mutant F A strain protein has a nucleotide sequence of SEQ ID NO: 6. In another embodiment, the mRNA comprising the ORF encoding RSV mutant F A strain protein further comprises a 5' untranslated region (UTR), a 3' UTR, and a poly (A) tail so as to have the structure of 5'UTR-ORF encoding RSV mutant F A strain protein-3'UTR-poly (A) tail, and the ORF encoding RSV mutant F A strain protein has a nucleotide sequence of SEQ ID NO: 6. In one embodiment, the poly (A) tail has a length of 50-250 nucleotides. In one embodiment, the mRNA having the structure of 5'UTR-ORF encoding RSV mutant F A strain protein-3'UTR-poly (A) tail has a nucleotide sequence of SEQ ID NO: 7. In another embodiment, the mRNA having the structure of 5'UTR-ORF encoding RSV mutant F A strain protein-3'UTR-poly (A) tail has a nucleotide sequence having at least 80% identity to SEQ ID NO: 7.

In one embodiment, the RSV vaccine composition of the present disclosure further comprises a pharmaceutically acceptable carrier. In one embodiment, the pharmaceutically acceptable carrier is a lipid nanoparticle encapsulating the mRNA therein.

The present disclosure also provides a method of inducing immune response against respiratory syncytial virus (RSV) comprising administering an effective amount of the RSV vaccine composition of the present disclosure to a subject in need thereof.

In addition, the present disclosure provides a respiratory syncytial virus (RSV) and human metapneumovirus virus (hMPV) vaccine composition comprising a messenger ribonucleic acid (mRNA) comprising an open reading frame (ORF) encoding RSV mutant F A strain protein having an amino acid sequence of SEQ ID NO: 5, a mRNA comprising an ORF encoding RSV mutant F B strain protein having an amino acid sequence of SEQ ID NO: 1, and a mRNA comprising an ORF encoding hMPV F protein having an amino acid sequence of SEQ ID NO: 9. In one embodiment, the ORF encoding RSV mutant F A strain protein has a nucleotide sequence of SEQ ID NO: 6, the ORF encoding RSV mutant F B strain protein has a nucleotide sequence of SEQ ID NO: 2, and the ORF encoding hMPV F protein has a nucleotide sequence of SEQ ID NO: 10. In another embodiment, the mRNA comprising the ORF encoding RSV mutant F A strain protein further comprises a 5' untranslated region (UTR), a 3' UTR, and a poly (A) tail so as to have the structure of 5'UTR-ORF encoding RSV mutant F A strain protein-3'UTR-poly (A) tail, and the ORF encoding RSV mutant F A strain protein has a nucleotide sequence of SEQ ID NO: 6. In one embodiment, the mRNA comprising the ORF encoding RSV mutant F B strain protein further comprises a 5' untranslated region (UTR), a 3' UTR, and a poly (A) tail so as to have the structure of 5'UTR-ORF encoding RSV mutant F B strain protein-3'UTR-poly (A) tail, and the ORF encoding RSV mutant F B strain protein has a nucleotide sequence of SEQ ID NO: 2. In another embodiment, the mRNA comprising the ORF encoding hMPV F protein further comprises a 5' untranslated region (UTR), a 3' UTR, and a poly (A) tail so as to have the structure of 5'UTR-ORF encoding hMPV F protein-3'UTR-poly (A) tail, and the ORF encoding hMPV F protein has a nucleotide sequence of SEQ ID NO: 10. In one embodiment, the poly (A) tail has a length of 50-250 nucleotides. In some embodiment, the mRNA having the structure of 5'UTR-ORF encoding RSV mutant F A strain protein-3'UTR-poly (A) tail has a nucleotide sequence of SEQ ID NO: 7. In some embodiment, the mRNA having the structure of 5'UTR-ORF encoding RSV mutant F B strain protein-3'UTR-poly (A) tail has a nucleotide sequence of SEQ ID NO: 3. In another embodiment, the mRNA having the structure of 5'UTR-ORF encoding hMPV F protein-3'UTR-poly (A) tail has a nucleotide sequence of SEQ ID NO: 11. In some embodiment, the mRNA having the structure of 5'UTR-ORF encoding RSV mutant F A strain protein-3'UTR-poly (A) tail has a nucleotide sequence having at least 80% identity to SEQ ID NO: 7. In another embodiment, the mRNA having the structure of 5'UTR-ORF encoding RSV mutant F B strain protein-3'UTR-poly (A) tail has a nucleotide sequence having at least 80% identity to SEQ ID NO: 3. In some embodiment, the mRNA having the structure of 5'UTR-ORF encoding hMPV F protein-3'UTR-poly (A) tail has a nucleotide sequence having at least 80% identity to SEQ ID NO: 11.

In some embodiment, the RSV and hMPV vaccine composition according to the present disclosure further comprises a pharmaceutically acceptable carrier. In another embodiment, the pharmaceutically acceptable carrier is a lipid nanoparticle encapsulating the mRNA therein.

The present disclosure also provides a method of inducing immune response against respiratory syncytial virus (RSV) and human metapneumovirus virus (hMPV) comprising administering an effective amount of the RSV and hMPV vaccine composition of the present disclosure to a subject in need thereof.

DEFINITIONS

Figure 1:
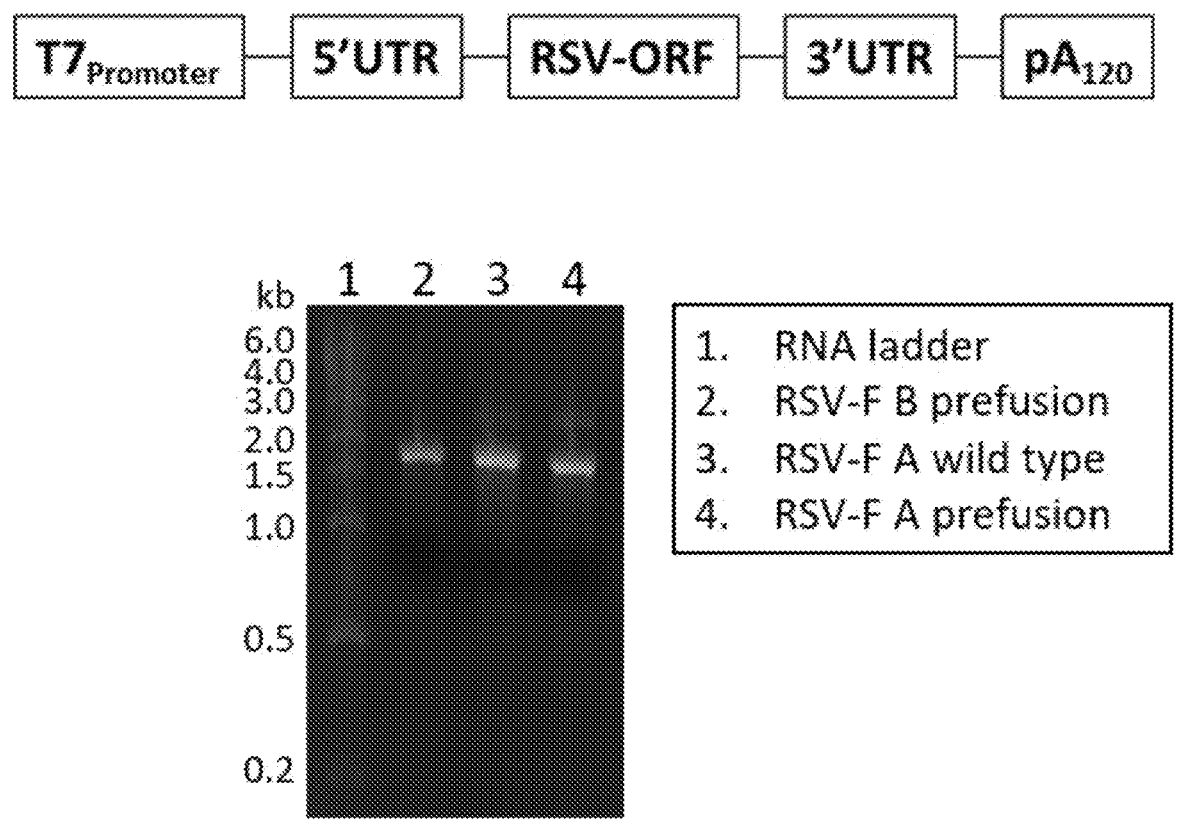
FIG. 1 shows the results of RSV-F IVT.

Although any methods and materials similar or equivalent to those described herein can be used in the practice or testing of embodiments described herein, some preferred methods, compositions, devices, and materials are described herein. However, before the present materials and methods are described, it is to be understood that this disclosure is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this disclosure belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise.

As used herein, the term "comprise" and linguistic variations thereof denote the presence of recited feature(s), element(s), method step(s), etc., without the exclusion of the presence of additional feature(s), element(s), method step(s), etc. Conversely, the term "consisting of" and linguistic variations thereof, denotes the presence of recited feature(s), element(s), method step(s), etc., and excludes any unrecited feature(s), element(s), method step(s), etc., except for ordinarily-associated impurities. The phrase "consisting essentially of" denotes the recited feature(s), element(s), method step(s), etc., and any additional feature(s), element(s), method step(s), etc., that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "respiratory syncytial virus (RSV) vaccine composition" refers to a substance used to stimulate the production of antibodies and provide immunity against RSV.

As used herein, the term "respiratory syncytial virus (RSV) and human metapneumovirus virus (hMPV) vaccine composition" refers to a substance used to stimulate the production of antibodies and provide immunity against RSV and hMPV.

As used herein, the term "messenger ribonucleic acid (mRNA)" refers to a single-stranded molecule of RNA that corresponds to the genetic sequence of a gene, and is read by a ribosome in the process of synthesizing a protein.

As used herein, the term "wild type" refers to a gene or gene product which has the characteristics of that gene or gene product when isolated from a naturally occurring source. In contrast, the term "modified" or "mutant" refers to a gene or gene product which displays altered characteristics when compared to the wild type gene or gene product. For example, a mutant DNA polymerase in the present invention is a DNA polymerase which exhibits a reduced uracil detection activity.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

As used herein, the term "open reading frame (ORF)" refers to a nucleotide sequence between the start and stop codons.

As used herein, the term "an open reading frame (ORF) encoding" refers to the nucleotide coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

As used herein, the term "T7 promoter" refers to a promoter derived from a bacteriophage T7.

As used herein, the term "5' untranslated region (UTR)" refers to a region of an mRNA that is directly upstream (i.e., 5') from the start codon (the first codon of an mRNA transcript translated by a ribosome) that does not encode a polypeptide.

As used herein, the term "3' untranslated region (UTR)" refers to a region of an mRNA that is directly downstream (i.e., 3') from the stop codon (i.e., the codon of an mRNA transcript that signals a termination of translation) that does not encode a polypeptide.

As used herein, the term "poly (A) tail" refers to a long stretch of adenine nucleotides added to the "tail" or 3' end of the mRNA.

As used herein, the term "pharmaceutically acceptable carrier" refers to any substance or vehicle suitable for delivering a mRNA vaccine to a suitable in vivo or ex vivo site. Such a carrier can include, but is not limited to, an adjuvant, an excipient, a lipid particle, etc.

As used herein, the term "lipid nanoparticle" refers to a particle having at least one dimension on the order of nanometers (e.g., 1-1,000 nm). In some embodiments, lipid nanoparticles are included in a formulation that can be used to deliver a mRNA vaccine to a target site of interest (e.g., cell, tissue, organ, tumor, and the like). In some embodiments, the mRNA vaccine, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response. In some embodiments, the lipid nanoparticle has a mean diameter of 50-200 nm. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

As used herein, the term "inducing immune response against respiratory syncytial virus (RSV)" refers to providing protective immunity and/or vaccinating a subject against a RSV infection for prophylactic purposes, as well as causing a desired immune response or effect in a subject in need thereof against a RSV infection, for therapeutic purposes. As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all.

An "effective amount" of the RSV vaccine composition (e.g. mRNA) or the RSV and hMPV vaccine composition is provided based, at least in part, on the target tissue, target cell type, means of administration, physical characteristics of the polynucleotide (e.g., size, and extent of modified nucleosides) and other components of the vaccine, and other determinants. In general, an effective amount of the RSV vaccine (e.g., mRNA) or the RSV and hMPV vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA, e.g., mRNA, vaccine), increased protein translation from the polynucleotide, decreased nucleic acid degradation (as demonstrated, for example, by increased duration of protein translation from a modified polynucleotide), or altered antigen specific immune response of the host cell.

As used herein, the term "X % identity to SEQ ID NO: Y" or "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "nucleotide sequence having at least X % identity to SEQ ID NO: Y and encodes Z protein" means that the nucleotide sequence meets the two different requirements of having at least X % identity to SEQ ID NO: Y and encoding Z protein.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The terms "subject," "patient," "individual," and the like are used interchangeably herein, and refer to any animal, any mammalian subject, or cells thereof whether in vitro or in situ, amenable to the methods described herein. In certain non-limiting embodiments, the patient, subject or individual is a human.

DETAILED DESCRIPTION

1. The Respiratory Syncytial Virus (RSV) Vaccine Composition, or the RSV and Human Metapneumovirus Virus (hMPV) Vaccine Composition The present disclosure provides a respiratory syncytial virus (RSV) vaccine composition comprising a messenger ribonucleic acid (mRNA) comprising an open reading frame (ORF) encoding RSV mutant F B strain protein having an amino acid sequence of SEQ ID NO: 1.

In the RSV vaccine composition, the RSV mutant F B strain protein may have an amino acid sequence having at least 80% identity to SEQ ID NO: 1. In another embodiment, the RSV mutant F B strain protein has an amino acid sequence having at least 85% identity to SEQ ID NO: 1. In another embodiment, the RSV mutant F B strain protein has an amino acid sequence having at least 90% identity to SEQ ID NO: 1. In another embodiment, the RSV mutant F B strain protein has an amino acid sequence having at least 95% identity to SEQ ID NO: 1. In another embodiment, the RSV mutant F B strain protein has an amino acid sequence having at least 96% identity to SEQ ID NO: 1. In another embodiment, the RSV mutant F B strain protein has an amino acid sequence having at least 97% identity to SEQ ID NO: 1. In another embodiment, the RSV mutant F B strain protein has an amino acid sequence having at least 98% identity to SEQ ID NO: 1. In another embodiment, the RSV mutant F B strain protein has an amino acid sequence having at least 99% identity to SEQ ID NO: 1.

In the RSV vaccine composition, the mRNA comprising the ORF encoding RSV mutant F B strain protein may further comprise a 5' untranslated region (UTR), a 3' UTR, and a poly (A) tail so as to have the structure of 5'UTR-ORF encoding RSV mutant F B strain protein-3'UTR-poly (A) tail, and the ORF encoding RSV mutant F B strain protein may have a nucleotide sequence of SEQ ID NO: 2 (or a nucleotide sequence having at least 80%, 85%, 90%, 95%, 96%, 97%, 98%, 99% or 99% identity to SEQ ID NO: 2).

In the RSV vaccine composition, the mRNA having the structure of 5'UTR-ORF encoding RSV mutant F B strain protein-3'UTR-poly (A) tail may have a nucleotide sequence of SEQ ID NO: 3 (or a nucleotide sequence having at least 80%, 85%, 90%, 95%, 96%, 97%, 98%, 99% or 99% identity to SEQ ID NO: 3).

The present disclosure also provides a RSV vaccine composition comprising a mRNA comprising an ORF encoding RSV mutant F B strain protein having an amino acid sequence of SEQ ID NO: 1, and a mRNA comprising an ORF encoding RSV mutant F A strain protein having an amino acid sequence of SEQ ID NO: 5. The above RSV vaccine composition, comprising both the mRNA encoding the ORF for the RSV mutant F B strain protein and the mRNA encoding the ORF for the RSV mutant F A strain protein, offers greater protection against the RSV mutant F B strain compared to the RSV vaccine composition containing only the mRNA encoding the ORF for the RSV mutant F A strain protein. The latter provides protective efficacy against the RSV mutant F B strain solely based on cross-reactivity.

In the RSV vaccine composition, the RSV mutant F A strain protein may have an amino acid sequence having at least 80% identity to SEQ ID NO: 5. In another embodiment, the RSV mutant F A strain protein has an amino acid sequence having at least 85% identity to SEQ ID NO: 5. In another embodiment, the RSV mutant F A strain protein has an amino acid sequence having at least 90% identity to SEQ ID NO: 5. In another embodiment, the RSV mutant F A strain protein has an amino acid sequence having at least 95% identity to SEQ ID NO: 5. In another embodiment, the RSV mutant F A strain protein has an amino acid sequence having at least 96% identity to SEQ ID NO: 5. In another embodiment, the RSV mutant F A strain protein has an amino acid sequence having at least 97% identity to SEQ ID NO: 5. In another embodiment, the RSV mutant F A strain protein has an amino acid sequence having at least 98% identity to SEQ ID NO: 5. In another embodiment, the RSV mutant F A strain protein has an amino acid sequence having at least 99% identity to SEQ ID NO: 5.

In the RSV vaccine composition, the mRNA comprising the ORF encoding RSV mutant F A strain protein may further comprise a 5' untranslated region (UTR), a 3' UTR, and a poly (A) tail so as to have the structure of 5'UTR-ORF encoding RSV mutant F A strain protein-3'UTR-poly (A) tail, and the ORF encoding RSV mutant F A strain protein may have a nucleotide sequence of SEQ ID NO: 6 (or a nucleotide sequence having at least 80%, 85%, 90%, 95%, 96%, 97%, 98%, 99% or 99% identity to SEQ ID NO: 6).

In the RSV vaccine composition, the mRNA having the structure of 5'UTR-ORF encoding RSV mutant F A strain protein-3'UTR-poly (A) tail may have a nucleotide sequence of SEQ ID NO: 7 (or a nucleotide sequence having at least 80%, 85%, 90%, 95%, 96%, 97%, 98%, 99% or 99% identity to SEQ ID NO: 7).

The present disclosure also provides a respiratory syncytial virus (RSV) and human metapneumovirus virus (hMPV) vaccine composition comprising a messenger ribonucleic acid (mRNA) comprising an open reading frame (ORF) encoding RSV mutant F A strain protein having an amino acid sequence of SEQ ID NO: 5, a mRNA comprising an ORF encoding RSV mutant F B strain protein having an amino acid sequence of SEQ ID NO: 1, and a mRNA comprising an ORF encoding hMPV F protein having an amino acid sequence of SEQ ID NO: 9.

In the RSV and hMPV vaccine composition, the RSV mutant F A strain protein may have an amino acid sequence having at least 80% identity to SEQ ID NO: 5. In another embodiment, the RSV mutant F A strain protein has an amino acid sequence having at least 85% identity to SEQ ID NO: 5. In another embodiment, the RSV mutant F A strain protein has an amino acid sequence having at least 90% identity to SEQ ID NO: 5. In another embodiment, the RSV mutant F A strain protein has an amino acid sequence having at least 95% identity to SEQ ID NO: 5. In another embodiment, the RSV mutant F A strain protein has an amino acid sequence having at least 96% identity to SEQ ID NO: 5. In another embodiment, the RSV mutant F A strain protein has an amino acid sequence having at least 97% identity to SEQ ID NO: 5. In another embodiment, the RSV mutant F A strain protein has an amino acid sequence having at least 98% identity to SEQ ID NO: 5. In another embodiment, the RSV mutant F A strain protein has an amino acid sequence having at least 99% identity to SEQ ID NO: 5.

In the RSV and hMPV vaccine composition, the RSV mutant F B strain protein may have an amino acid sequence having at least 80% identity to SEQ ID NO: 1. In another embodiment, the RSV mutant F B strain protein has an amino acid sequence having at least 85% identity to SEQ ID NO: 1. In another embodiment, the RSV mutant F B strain protein has an amino acid sequence having at least 90% identity to SEQ ID NO: 1. In another embodiment, the RSV mutant F B strain protein has an amino acid sequence having at least 95% identity to SEQ ID NO: 1. In another embodiment, the RSV mutant F B strain protein has an amino acid sequence having at least 96% identity to SEQ ID NO: 1. In another embodiment, the RSV mutant F B strain protein has an amino acid sequence having at least 97% identity to SEQ ID NO: 1. In another embodiment, the RSV mutant F B strain protein has an amino acid sequence having at least 98% identity to SEQ ID NO: 1. In another embodiment, the RSV mutant F B strain protein has an amino acid sequence having at least 99% identity to SEQ ID NO: 1.

In the RSV and hMPV vaccine composition, the hMPV F protein may have an amino acid sequence having at least 80% identity to SEQ ID NO: 9. In another embodiment, the hMPV F protein has an amino acid sequence having at least 85% identity to SEQ ID NO: 9. In another embodiment, the hMPV F protein has an amino acid sequence having at least 90% identity to SEQ ID NO: 9. In another embodiment, the hMPV F protein has an amino acid sequence having at least 95% identity to SEQ ID NO: 9. In another embodiment, the hMPV F protein has an amino acid sequence having at least 96% identity to SEQ ID NO: 9. In another embodiment, the hMPV F protein has an amino acid sequence having at least 97% identity to SEQ ID NO: 9. In another embodiment, the hMPV F protein has an amino acid sequence having at least 98% identity to SEQ ID NO: 9. In another embodiment, the hMPV F protein has an amino acid sequence having at least 99% identity to SEQ ID NO: 9.

In one embodiment, the ORF encoding RSV mutant F A strain protein has a nucleotide sequence of SEQ ID NO: 6, the ORF encoding RSV mutant F B strain protein has a nucleotide sequence of SEQ ID NO: 2, and the ORF encoding hMPV F protein has a nucleotide sequence of SEQ ID NO: 10. In another embodiment, the mRNA comprising the ORF encoding RSV mutant F A strain protein further comprises a 5' untranslated region (UTR), a 3' UTR, and a poly (A) tail so as to have the structure of 5'UTR-ORF encoding RSV mutant F A strain protein-3'UTR-poly (A) tail, and the ORF encoding RSV mutant F A strain protein has a nucleotide sequence of SEQ ID NO: 6. In one embodiment, the mRNA comprising the ORF encoding RSV mutant F B strain protein further comprises a 5' untranslated region (UTR), a 3' UTR, and a poly (A) tail so as to have the structure of 5'UTR-ORF encoding RSV mutant F B strain protein-3'UTR-poly (A) tail, and the ORF encoding RSV mutant F B strain protein has a nucleotide sequence of SEQ ID NO: 2. In another embodiment, the mRNA comprising the ORF encoding hMPV F protein further comprises a 5' untranslated region (UTR), a 3' UTR, and a poly (A) tail so as to have the structure of 5'UTR-ORF encoding hMPV F protein-3'UTR-poly (A) tail, and the ORF encoding hMPV F protein has a nucleotide sequence of SEQ ID NO: 10.

In the RSV and hMPV vaccine composition, the ORF encoding RSV mutant F A strain protein may have a nucleotide sequence having at least 80% identity to SEQ ID NO: 6. In another embodiment, the ORF encoding RSV mutant F A strain protein may have a nucleotide sequence having at least 85% identity to SEQ ID NO: 6. In another embodiment, the ORF encoding RSV mutant F A strain protein may have a nucleotide sequence having at least 90% identity to SEQ ID NO: 6. In another embodiment, the ORF encoding RSV mutant F A strain protein may have a nucleotide sequence having at least 95% identity to SEQ ID NO: 6. In another embodiment, the ORF encoding RSV mutant F A strain protein may have a nucleotide sequence having at least 96% identity to SEQ ID NO: 6. In another embodiment, the ORF encoding RSV mutant F A strain protein may have a nucleotide sequence having at least 97% identity to SEQ ID NO: 6. In another embodiment, the ORF encoding RSV mutant F A strain protein may have a nucleotide sequence having at least 98% identity to SEQ ID NO: 6. In another embodiment, the ORF encoding RSV mutant F A strain protein may have a nucleotide sequence having at least 99% identity to SEQ ID NO: 6.

In the RSV and hMPV vaccine composition, the ORF encoding RSV mutant F B strain protein may have a nucleotide sequence having at least 80% identity to SEQ ID NO: 2. In another embodiment, the ORF encoding RSV mutant F B strain protein may have a nucleotide sequence having at least 85% identity to SEQ ID NO: 2. In another embodiment, the ORF encoding RSV mutant F B strain protein may have a nucleotide sequence having at least 90% identity to SEQ ID NO: 2. In another embodiment, the ORF encoding RSV mutant F B strain protein may have a nucleotide sequence having at least 95% identity to SEQ ID NO: 2. In another embodiment, the ORF encoding RSV mutant F B strain protein may have a nucleotide sequence having at least 96% identity to SEQ ID NO: 2. In another embodiment, the ORF encoding RSV mutant F B strain protein may have a nucleotide sequence having at least 97% identity to SEQ ID NO: 2. In another embodiment, the ORF encoding RSV mutant F B strain protein may have a nucleotide sequence having at least 98% identity to SEQ ID NO: 2. In another embodiment, the ORF encoding RSV mutant F B strain protein may have a nucleotide sequence having at least 99% identity to SEQ ID NO: 2.

In the RSV and hMPV vaccine composition, the ORF encoding hMPV F protein may have a nucleotide sequence having at least 80% identity to SEQ ID NO: 10. In another embodiment, the ORF encoding hMPV F protein may have a nucleotide sequence having at least 85% identity to SEQ ID NO: 10. In another embodiment, the ORF encoding hMPV F protein may have a nucleotide sequence having at least 90% identity to SEQ ID NO: 10. In another embodiment, the ORF encoding hMPV F protein may have a nucleotide sequence having at least 95% identity to SEQ ID NO: 10. In another embodiment, the ORF encoding hMPV F protein may have a nucleotide sequence having at least 96% identity to SEQ ID NO: 10. In another embodiment, the ORF encoding hMPV F protein may have a nucleotide sequence having at least 97% identity to SEQ ID NO: 10. In another embodiment, the ORF encoding hMPV F protein may have a nucleotide sequence having at least 98% identity to SEQ ID NO: 10. In another embodiment, the ORF encoding hMPV F protein may have a nucleotide sequence having at least 99% identity to SEQ ID NO: 10.

In one embodiment, the poly (A) tail has a length of 50-250 nucleotides. In some embodiment, the mRNA having the structure of 5'UTR-ORF encoding RSV mutant F A strain protein-3'UTR-poly (A) tail has a nucleotide sequence of SEQ ID NO: 7. In some embodiment, the mRNA having the structure of 5'UTR-ORF encoding RSV mutant F B strain protein-3'UTR-poly (A) tail has a nucleotide sequence of SEQ ID NO: 3. In another embodiment, the mRNA having the structure of 5'UTR-ORF encoding hMPV F protein-3'UTR-poly (A) tail has a nucleotide sequence of SEQ ID NO: 11. In some embodiment, the mRNA having the structure of 5'UTR-ORF encoding RSV mutant F A strain protein-3'UTR-poly (A) tail has a nucleotide sequence having at least 80% identity to SEQ ID NO: 7 (or a nucleotide sequence having at least 85%, 90%, 95%, 96%, 97%, 98%, 99% or 99% identity to SEQ ID NO: 7). In another embodiment, the mRNA having the structure of 5'UTR-ORF encoding RSV mutant F B strain protein-3'UTR-poly (A) tail has a nucleotide sequence having at least 80% identity to SEQ ID NO: 3 (or a nucleotide sequence having at least 85%, 90%, 95%, 96%, 97%, 98%, 99% or 99% identity to SEQ ID NO: 3). In some embodiment, the mRNA having the structure of 5'UTR-ORF encoding hMPV F protein-3'UTR-poly (A) tail has a nucleotide sequence having at least 80% identity to SEQ ID NO: 11 (or a nucleotide sequence having at least 85%, 90%, 95%, 96%, 97%, 98%, 99% or 99% identity to SEQ ID NO: 11).

In one embodiment, the poly (A) tail has a length of 50-250 nucleotides. In another embodiment, the poly (A) tail has a length of 100-200 nucleotides. In another embodiment, the poly (A) tail has a length of 110-150 nucleotides. In another embodiment, the poly (A) tail has a length of 115-125 nucleotides. In another embodiment, the poly (A) tail has a length of 116-124 nucleotides. In another embodiment, the poly (A) tail has a length of 117-123 nucleotides. In another embodiment, the poly (A) tail has a length of 118-122 nucleotides. In another embodiment, the poly (A) tail has a length of 119-122 nucleotides. In another embodiment, the poly (A) tail has a length of 115 nucleotides. In another embodiment, the poly (A) tail has a length of 116 nucleotides. In another embodiment, the poly (A) tail has a length of 117 nucleotides. In another embodiment, the poly (A) tail has a length of 118 nucleotides. In another embodiment, the poly (A) tail has a length of 119 nucleotides. In another embodiment, the poly (A) tail has a length of 120 nucleotides. In another embodiment, the poly (A) tail has a length of 121 nucleotides. In another embodiment, the poly (A) tail has a length of 122 nucleotides. In another embodiment, the poly (A) tail has a length of 123 nucleotides. In another embodiment, the poly (A) tail has a length of 124 nucleotides. In another embodiment, the poly (A) tail has a length of 125 nucleotides.

In one embodiment, the mRNA of the present disclosure may comprise at least one chemical modification selected from the group consisting of pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In another embodiment, the chemical modification is in the 5-position of the uracil. In another embodiment, the chemical modification is a N1-methylpseudouridine. In another embodiments, the chemical modification is a N1-ethylpseudouridine.

In one embodiment, the RSV vaccine composition further comprises a pharmaceutically acceptable carrier. In another embodiment, the pharmaceutically acceptable carrier may include any substance or vehicle suitable for delivering a mRNA vaccine to a suitable in vivo or ex vivo site. Such a carrier can include, but is not limited to, an adjuvant, an excipient, a lipid particle, etc. The lipid nanoparticle may be a particle having at least one dimension on the order of nanometers (e.g., 1-1,000 nm). In some embodiments, lipid nanoparticles are included in a formulation that can be used to deliver a mRNA vaccine to a target site of interest (e.g., cell, tissue, organ, tumor, and the like). In some embodiments, the mRNA vaccine, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response. In some embodiments, the lipid nanoparticle has a mean diameter of 50-200 nm. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

In one embodiment, the lipid nanoparticle comprises (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), (ii) a neutral lipid selected from DSPC, DPPC, POPC, DOPE and SM, (iii) a sterol, e.g., cholesterol, and (iv) a PEG-lipid, e.g., PEG-DMG or PEG-CDMA, in a molar ratio of about 20-60% cationic lipid:5-25% neutral lipid:25-55% sterol; 0.5-15% PEG-lipid.

In one embodiment, the lipid nanoparticle includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about to about 65%, from about 45 to about 65%, about 60%, about 57.5%, about 50% or about 40% on a molar basis.

In one embodiment, the lipid nanoparticle includes from about 0.5% to about 15% on a molar basis of the neutral lipid e.g., from about 3 to about 12%, from about 5 to about 10% or about 15%, about 10%, or about 7.5% on a molar basis. Examples of neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Examples of PEG-modified lipids include, but are not limited to, PEG-distearoyl glycerol (PEG-DMG) (also referred herein as PEG-C14 or C14-PEG), and PEG-cDMA.

In one embodiment, the lipid nanoparticle includes 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the lipid nanoparticle include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the lipid nanoparticle includes 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the lipid nanoparticle includes about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the lipid nanoparticle includes about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the lipid nanoparticle includes about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the lipid nanoparticle includes about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the RSV vaccine composition or the RSV and hMPV vaccine composition of the present disclosure may be delivered, localized and/or concentrated in a specific location using the delivery methods described as follows. As a non-limiting example, a subject may be administered an empty polymeric particle prior to, simultaneously with or after delivering the RSV vaccine composition of the present disclosure to the subject. The empty polymeric particle undergoes a change in volume once in contact with the subject and becomes lodged, embedded, immobilized or entrapped at a specific location in the subject.

In another embodiment, the RSV vaccine composition of the present disclosure may be formulated in an active substance release system. For instance, the active substance release system may comprise at least one nanoparticle bonded to an oligonucleotide inhibitor strand which is hybridized with a catalytically active nucleic acid and a compound bonded to at least one substrate molecule bonded to a therapeutically active substance (e.g., polynucleotides described herein), where the therapeutically active substance is released by the cleavage of the substrate molecule by the catalytically active nucleic acid.

In another embodiment, the RSV vaccine composition or the RSV and hMPV vaccine composition of the present disclosure may be formulated in a nanoparticle comprising an inner core comprising a non-cellular material and an outer surface comprising a cellular membrane. The cellular membrane may be derived from a cell or a membrane derived from a virus.

In another embodiment, the RSV vaccine composition or the RSV and hMPV vaccine composition of the present disclosure may be formulated in porous nanoparticle-supported lipid bilayers (protocells).

In another embodiment, the RSV vaccine composition or the RSV and hMPV vaccine composition of the present disclosure may be formulated in polymeric nanoparticles which have a high glass transition temperature.

In another embodiment, the RSV vaccine composition or the RSV and hMPV vaccine composition of the present disclosure may be formulated in nanoparticles used in imaging. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component.

The nanoparticles of the present disclosure may further include nutrients such as, but not limited to, those which deficiencies can lead to health hazards from anemia to neural tube defects. As a non-limiting example, the nutrient may be iron in the form of ferrous, ferric salts or elemental iron, iodine, folic acid, vitamins or micronutrients.

In another embodiment, the RSV vaccine composition or the RSV and hMPV vaccine composition of the present disclosure may be formulated in a swellable nanoparticle.

In another embodiment, the RSV vaccine composition or the RSV and hMPV vaccine composition of the present disclosure may be formulated in polyanhydride nanoparticles.

The nanoparticles and microparticles of the present disclosure may be geometrically engineered to modulate macrophage and/or the immune response. In some embodiments, the geometrically engineered particles may have varied shapes, sizes and/or surface charges in order to incorporated the polynucleotides of the present disclosure for targeted delivery such as, but not limited to, pulmonary delivery. Other physical features the geometrically engineering particles may have include, but are not limited to, fenestrations, angled arms, asymmetry and surface roughness, charge which can alter the interactions with cells and tissues.

In another embodiment, the nanoparticles of the present disclosure may be water soluble nanoparticles. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments, the nanoparticles of the present disclosure are stealth nanoparticles or target-specific stealth nanoparticles. In some embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle of the present disclosure may be a nanoparticle-nucleic acid hybrid structure having a high density nucleic acid layer. The nanoparticle of the present disclosure may comprise a nucleic acid such as, but not limited to, polynucleotides described herein and/or known in the art.

In one embodiment, at least one of the nanoparticles of the present disclosure may be embedded in in the core a nanostructure or coated with a low density porous 3-D structure or coating which is capable of carrying or associating with at least one payload within or on the surface of the nanostructure.

In one embodiment, the pharmaceutically acceptable carrier is a lipid nanoparticle encapsulating the mRNAs of the present disclosure therein.

2. The Method of Inducing Immune Response Against Respiratory Syncytial Virus (RSV), or the Method of Inducing Immune Response Against RSV and Human Metapneumovirus Virus (hMPV)

The present disclosure also provides a method of inducing immune response against respiratory syncytial virus (RSV) comprising administering an effective amount of the RSV vaccine composition of the present disclosure a subject in need thereof.

The present disclosure also provides a method of inducing immune response against RSV and human metapneumovirus virus (hMPV) comprising administering an effective amount of the RSV and hMPV vaccine composition of the present disclosure a subject in need thereof.

In one embodiment, the effective amount of the RSV vaccine composition or the RSV and hMPV vaccine composition (e.g. mRNA) is provided based, at least in part, on the target tissue, target cell type, means of administration, physical characteristics of the polynucleotide (e.g., size, and extent of modified nucleosides) and other components of the vaccine, and other determinants. In general, an effective amount of the RSV vaccine the RSV and hMPV vaccine composition (e.g., mRNA) provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA, e.g., mRNA, vaccine), increased protein translation from the polynucleotide, decreased nucleic acid degradation (as demonstrated, for example, by increased duration of protein translation from a modified polynucleotide), or altered antigen specific immune response of the host cell.

Administration of an effective amount (immunogenically effective amount) of the RSV vaccine composition the RSV and hMPV vaccine composition is typically intramuscular or subcutaneous. Thus, the RSV vaccine composition is typically formulated for intramuscular or subcutaneous injection, and for the purposes of the invention formulated without adjuvants, preferably without any adjuvant. However other modes of administration, such as intravenous, cutaneous, intradermal or nasal can be envisaged as well. For intravenous, cutaneous or subcutaneous injection, the adenovirus vector will be in the form of a parenterally acceptable aqueous solution which is pyrogen-free and has suitable pH, isotonicity and stability. Likewise, the isolated envelope polypeptide will be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In a particular embodiment, an effective amount (immunogenically effective amount) of the RSV vaccine composition the RSV and hMPV vaccine composition is administered via intramuscular administration. Intramuscular administration can be achieved by using a needle to inject a suspension of the adenovirus vectors and/or envelope polypeptides. An alternative is the use of a needleless injection device to administer the composition (using, e.g., Biojector™) or a freeze-dried powder containing the vaccine.

In one embodiment, the priming immunization and/or the boosting administration, preferably both the priming and boosting administration, further comprise administering one or more adenovirus vectors that encode one or more further RSV antigens or RSV and hMPV antigens.

The timing for administering priming and boosting immunizations is not particularly limited. For example, a vaccine composition can be administered for priming immunization, and re-administered prior to administration of a vaccine composition for boosting immunization. Further administrations of a vaccine composition for further boosting immunizations are also contemplated. In certain embodiments, a booster vaccine is first administered about 1-12 weeks, e.g., 1, 2, 3, 4, 5, 6, 7, 8, 9, 10, 11, or 12 weeks after a primer vaccine is initially administered. In other embodiments, a booster vaccine is first administered about 12-52 weeks, e.g., about 12, 14, 16, 18, 20, 22, 24, 26, 28, 30, 32, 34, 36, 38, 40, 42, 44, 46, 48, 50, or 52 weeks after a primer vaccine is initially administered. One of ordinary skill in the art will be able to vary the exact timing of the priming and boosting vaccines, frequency of administration thereof, dosage thereof, etc., based upon the teachings herein and general knowledge in the art.

In one embodiment, the RSV vaccine composition or the RSV and hMPV vaccine composition may comprise the first and second mRNAs described herein, formulated in a lipid nanoparticle comprising MC3, Cholesterol, DSPC and PEG2000-DMG, the buffer trisodium citrate, sucrose and water for injection. As a non-limiting example, the composition may comprise 2.0 mg/mL of drug substance, 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In one embodiment, the method of inducing immune response against RSV comprises administering an effective amount of the RSV vaccine composition of the present disclosure to a subject in need thereof. In the RSV vaccine composition, the mRNA having the structure of 5'UTR-ORF encoding RSV mutant F B strain protein-3'UTR-poly (A) tail may have a nucleotide sequence of SEQ ID NO: 3 (or a nucleotide sequence having at least 80%, 85%, 90%, 95%, 96%, 97%, 98%, 99% or 99% identity to SEQ ID NO: 3).

In another embodiment, the RSV vaccine composition comprises a mRNA having the structure of 5'UTR-ORF encoding RSV mutant F B strain protein-3'UTR-poly (A) tail may have a nucleotide sequence of SEQ ID NO: 3 (or a nucleotide sequence having at least 80%, 85%, 90%, 95%, 96%, 97%, 98%, 99% or 99% identity to SEQ ID NO: 3), and a mRNA having the structure of 5'UTR-ORF encoding RSV mutant F A strain protein-3'UTR-poly (A) tail may have a nucleotide sequence of SEQ ID NO: 7 (or a nucleotide sequence having at least 80%, 85%, 90%, 95%, 96%, 97%, 98%, 99% or 99% identity to SEQ ID NO: 7).

In another embodiment, the method of inducing immune response against RSV and hMPV comprises administering an effective amount of the RSV and hMPV vaccine composition of the present disclosure to a subject in need thereof. In the RSV and hMPV vaccine composition, the mRNA having the structure of 5'UTR-ORF encoding RSV mutant F A strain protein-3'UTR-poly (A) tail may have a nucleotide sequence of SEQ ID NO: 7 (or a nucleotide sequence having at least 80%, 85%, 90%, 95%, 96%, 97%, 98%, 99% or 99% identity to SEQ ID NO: 7). In addition, the mRNA having the structure of 5'UTR-ORF encoding RSV mutant F B strain protein-3'UTR-poly (A) tail may have a nucleotide sequence of SEQ ID NO: 3 (or a nucleotide sequence having at least 80%, 85%, 90%, 95%, 96%, 97%, 98%, 99% or 99% identity to SEQ ID NO: 3). Moreover, the mRNA having the structure of 5'UTR-ORF encoding hMPV protein-3'UTR-poly (A) tail may have a nucleotide sequence of SEQ ID NO: 11 (or a nucleotide sequence having at least 80%, 85%, 90%, 95%, 96%, 97%, 98%, 99% or 99% identity to SEQ ID NO: 11).

3. Sequence Information

```
1) Protein sequence of the ORF encoded in RSV mutant F B strain mRNA
SEQ ID NO: 1
MELLIHRSSAIFLTLAINALYLTSSQNITEEFYQSTCSAVSRGYLSALRTGWYTSVITIELS
NIKETKCNGTDTKVKLIKQELDKYKNAVTELQLLMQNTPAVNNRARREAPQYMNYTIN
TTKNLNVSISKKRKRRFLGFLLGVGSAIASGIAVCKVLHLEGEVNKIKNALQLTNKAVVS
LSNGVSVLTFRVLDLKNYINNQLLPMLNRQSCRISNIETVIEFQQKNSRLLEITREFSVNA
GVTTPLSTYMLTNSELLSLINDMPITNDQKKLMSSNVQIVRQQSYSIMCIIKEEVLAYVV
QLPIYGVIDTPCWKLHTSPLCTTNIKEGSNICLTRTDRGWYCDNAGSVSFFPQADTCKVQ
SNRVFCDTMNSLTLPSEVSLCNTDIFNSKYDCKIMTSKTDISSSVITSLGAIVSCYGKTKC
TASNKNRGIIKTFSNGCDYVSNKGVDTVSVGNTLYYVNKLEGKNLYVKGEPIINYYDPL
VFPSDEFDASISQVNEKINQSLAFIRRSDELLHNVNTGKSTTNIMITAIIIVIIVVLLSLIAIGL
LLYCKAKNTPVTLSKDQLSGINNIAFSK 2) RSV mutant F B strain mRNA sequence (ORF)
SEQ ID NO: 2
AUGGAACUGCUGAUCCACAGAUCCAGCGCUAUUUUCCUGACACUGGCCAUCAAUG
CCCUGUACCUGACAAGCAGCCAGAACAUCACAGAGGAAUUCUACCAGAGUACCUG
UAGCGCUGUGUCUCGGGGAUACCUGAGCGCCCUGCGGACCGGUUGGUACACCAGC
GUGAUCACAAUCGAGCUGAGUAACAUCAAGGAGACAAAAUGCAAUGGCACUGAC
ACCAAGGUGAAACUUAUCAAACAGGAGCUGGAUAAGUACAAGAAUGCCGUGACA
GAACUGCAGCUGCUGAUGCAGAAUACCCCCGCCGUGAACAACAGAGCCAGACGGG
AAGCCCCUCAAUACAUGAACUACACAAUCAACACCACAAAGAACCUGAACGUGUC
UAUCUCCAAGAAGCGCAAGCGGAGAUUCCUGGGCUUCCUGUUGGGAGUGGGCUC
UGCCAUCGCCAGCGGCAUCGCAGUGUGCAAGGUGCUGCACCUGGAAGGAGAAGUG
AACAAGAUCAAGAAUGCCCUGCAGCUGACCAACAAGGCCGUGGUCUCUCUGAGCA
AUGGCGUGAGCGUGCUGACCUUUAGAGUGCUGGACCUGAAGAACUACAUCAACA
ACCAGCUGCUGCCUAUGCUGAACAGACAGUCUUGUAGAAUCAGCAACAUCGAAAC
CGUGAUCGAGUUCCAGCAGAAGAACUCCAGGCUGCUGGAAAUCACAAGAGAGUU
UAGCGUGAACGCCGGCGUCACCACCCCCCUGAGCACCUACAUGCUGACCAACAGC
```

GAGCUGCUGAGCCUGAUUAACGACAUGCCUAUCACCAAUGACCAGAAAAGCUAA
UGAGCAGCAAUGUGCAAAUCGUGCGGCAGCAGUCCUACAGCAUCAUGUGCAUCAU
CAAGGAAGAGGUCCUGGCCUACGUGGUACAACUGCCUAUCUACGGCGUGAUCGAC
ACCCCUUGUUGGAAGCUCCAUACCAGCCCUCUGUGCACAACAAACAUCAAAGAAG
GCAGCAAUAUCUGCCUGACAAGAACAGAUAGAGGCUGGUAUUGUGACAACGCUG
GCUCCGUCUCCUUCUUCCCUCAGGCCGACACCUGCAAGGUGCAGAGCAACCGCGU
GUUCUGCGAUACCAUGAACAGCUUAACACUGCCCAGCGAGGUGUCUCUCUGUAAC
ACCGACAUCUUCAACUCUAAAUACGACUGCAAGAUCAUGACCUCUAAGACUGAUA
UCAGCAGCAGCGUGAUUACCUCCCUGGGCGCCAUCGUGUCUUGCUACGGCAAGAC
AAAGUGCACCGCCAGCAACAAGAACCGGGGCAUCAUCAAGACCUUCAGCAACGGC
UGCGACUACGUGAGCAACAAGGGCGUGGACACCGUUAGCGUGGGCAACACACUGU
AUUACGUAAAUAAACUUGAGGGCAAGAAUCUGUACGUGAAGGGCGAGCCUAUCA
UCAACUACUACGACCCACUGGUGUUUCCAUCUGAUGAGUUCGACGCCUCCAUCUC
CCAGGUGAACGAGAAGAUCAACCAGAGCCUGGCUUUUAUCAGAAGAAGCGAUGA
GCUGCUGCACAACGUGAAUACCGGAAAAAGCACCACCAACAUCAUGAUCACCGCC
AUCAUUAUCGUUAUCAUCGUGGUGCUGCUAGUCUGAUCGCCAUUGGACUGCUG
CUGUAUUGCAAAGCCAAGAACACCCCCGUGACCCUGAGCAAGGACCAGCUGAGCG
GCAUCAACAACAUAGCUUUCUCCAAG

3) RSV mutant F B strain mRNA sequence (5'-UTR-ORF-3'UTR-Poly(A) tail)
SEQ ID NO: 3
AGGCCGGCACUCUUCUGGUCCCCACAGACUCAGAGAGAACCCGCCGCCACCAUGG
AACUGCUGAUCCACAGAUCCAGCGCUAUUUUCCUGACACUGGCCAUCAAUGCCCU
GUACCUGACAAGCAGCCAGAACAUCACAGAGGAAUUCUACCAGAGUACCUGUAGC
GCUGUGUCUCGGGGAUACCUGAGCGCCCUGCGGACCGGUUGGUACACCAGCGUGA
UCACAAUCGAGCUGAGUAACAUCAAGGAGACAAAAUGCAAUGGCACUGACACCA
AGGUGAAACUUAUCAAACAGGAGCUGGAUAAGUACAAGAAUGCCGUGACAGAAC
UGCAGCUGCUGAUGCAGAAUACCCCCGCCGUGAACAACAGAGCCAGACGGGAAGC
CCCUCAAUACAUGAACUACACAAUCAACACCACAAAGAACCUGAACGUGUCUAUC
UCCAAGAAGCGCAAGCGGAGAUUCCUGGGCUUCCUGUUGGGAGUGGGCUCUGCCA
UCGCCAGCGGCAUCGCAGUGUGCAAGGUGCUGCACCUGGAAGGAGAAGUGAACA
AGAUCAAGAAUGCCCUGCAGCUGACCAACAAGGCCGUGGUCUCUCUGAGCAAUGG
CGUGAGCGUGCUGACCUUUAGAGUGCUGGACCUGAAGAACUACAUCAACAACCAG
CUGCUGCCUAUGCUGAACAGACAGUCUUGUAGAAUCAGCAACAUCGAAACCGUGA
UCGAGUUCCAGCAGAAGAACUCCAGGCUGCUGGAAAUCACAAGAGAGUUUAGCG
UGAACGCCGGCGUCACCACCCCCUGAGCACCUACAUGCUGACCAACAGCGAGCU
GCUGAGCCUGAUUAACGACAUGCCUAUCACCAAUGACCAGAAAAAGCUAAUGAGC
AGCAAUGUGCAAAUCGUGCGGCAGCAGUCCUACAGCAUCAUGUGCAUCAUCAAGG
AAGAGGUCCUGGCCUACGUGGUACAACUGCCUAUCUACGGCGUGAUCGACACCCC
UUGUUGGAAGCUCCAUACCAGCCCUCUGUGCACAACAAACAUCAAAGAAGGCAGC
AAUAUCUGCCUGACAAGAACAGAUAGAGGCUGGUAUUGUGACAACGCUGGCUCC
GUCUCCUUCUUCCCUCAGGCCGACACCUGCAAGGUGCAGAGCAACCGCGUGUUCU
GCGAUACCAUGAACAGCUUAACACUGCCCAGCGAGGUGUCUCUCUGUAACACCGA
CAUCUUCAACUCUAAAUACGACUGCAAGAUCAUGACCUCUAAGACUGAUAUCAGC
AGCAGCGUGAUUACCUCCCUGGGCGCCAUCGUGUCUUGCUACGGCAAGACAAAGU
GCACCGCCAGCAACAAGAACCGGGGCAUCAUCAAGACCUUCAGCAACGGCUGCGA
CUACGUGAGCAACAAGGGCGUGGACACCGUUAGCGUGGGCAACACACUGUAUUAC
GUAAAUAAACUUGAGGGCAAGAAUCUGUACGUGAAGGGCGAGCCUAUCAUCAAC
UACUACGACCCACUGGUGUUUCCAUCUGAUGAGUUCGACGCCUCCAUCUCCCAGG
UGAACGAGAAGAUCAACCAGAGCCUGGCUUUUAUCAGAAGAAGCGAUGAGCUGC
UGCACAACGUGAAUACCGGAAAAAGCACCACCAACAUCAUGAUCACCGCCAUCAU
UAUCGUUAUCAUCGUGGUGCUGCUAGAUCUGAUCGCCAUUGGACUGCUGCUGUA
UUGCAAAGCCAAGAACACCCCCGUGACCCUGAGCAAGGACCAGCUGAGCGGCAUC
AACAACAUAGCUUUCUCCAAGUGACUCGAGUAAGCUGGAGCCUCGGUGGCCAUGC
UUCUUGCCCCUUGGGCCUCCCCCCAGCCCCUCCUCCCCUUCCUGCACCCGUACCCC
CGUGGUCUUUGAAUAAAGUCUGAGUGGGCGGCAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA 4) Sequence of pUC57 plasmid encoding RSV mutant F B strain mRNA sequence
(mRNA sequence has been underlined)
SEQ ID NO: 4
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGTC
AGCGGGTGTTGGCGGGTGTCGGGGCTGGCTTAACTATGCGGCATCAGAGCAGATTG
TACTGAGAGTGCACCATATGCGGTGTGAAATACCGCACAGATGCGTAAGGAGAAAA
TACCGCATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GTGAATTCGAGCTCGGTACCTCGCGAATGCATCTAGATTCTAGATTAATACGACTCA
CTATAAGGCCGGCACTCTTCTGGTCCCCACAGACTCAGAGAGAACCCGCCGCCACC
ATGGAACTGCTGATCCACAGATCCAGCGCTATTTTCCTGACACTGGCCATCAATGCC
CTGTACCTGACAAGCAGCCAGAACATCACAGAGGAATTCTACCAGAGTACCTGTAG
CGCTGTGTCTCGGGGATACCTGAGCGCCCTGCGGACCGGTTGGTACACCAGCGTGAT
CACAATCGAGCTGAGTAACATCAAGGAGACAAAATGCAATGGCACTGACACCAAGG
TGAAACTTATCAAACAGGAGCTGGATAAGTACAAGAATGCCGTGACAGAACTGCAG
CTGCTGATGCAGAATACCCCCGCCGTGAACAACAGAGCCAGACGGGAAGCCCCTCA
ATACATGAACTACACAATCAACACCACAAAGAACCTGAACGTGTCTATCTCCAAGA
AGCGCAAGCGGAGATTCCTGGGCTTCCTGTTGGGAGTGGGCTCTGCCATCGCCAGCG -continued

```
GCATCGCAGTGTGCAAGGTGCTGCACCTGGAAGGAGAAGTGAACAAGATCAAGAAT
GCCCTGCAGCTGACCAACAAGGCCGTGGTCTCTCTGAGCAATGGCGTGAGCGTGCT
GACCTTTAGAGTGCTGGACCTGAAGAACTACATCAACAACCAGCTGCTGCCTATGCT
GAACAGACAGTCTTGTAGAATCAGCAACATCGAAACCGTGATCGAGTTCCAGCAGA
AGAACTCCAGGCTGCTGGAAATCACAAGAGAGTTTAGCGTGAACGCCGGCGTCACC
ACCCCCCTGAGCACCTACATGCTGACCAACAGCGAGCTGCTGAGCCTGATTAACGA
CATGCCTATCACCAATGACCAGAAAAAGCTAATGAGCAGCAATGTGCAAATCGTGC
GGCAGCAGTCCTACAGCATCATGTGCATCATCAAGGAAGAGGTCCTGGCCTACGTG
GTACAACTGCCTATCTACGGCGTGATCGACACCCCTTGTTGGAAGCTCCATACCAGC
CCTCTGTGCACAACAAACATCAAAGAAGGCAGCAATATCTGCCTGACAAGAACCAGA
TAGAGGCTGGTATTGTGACAACGCTGGCTCCGTCTCCTTCTTCCCTCAGGCCGACAC
CTGCAAGGTGCAGAGCAACCGCGTGTTCTGCGATACCATGAACAGCTTAACACTGC
CCAGCGAGGTGTCTCTGTAACACCGACATCTTCAACTCTAAATACGACTGCAAGA
TCATGACCTCTAAGACTGATATCAGCAGCAGCGTGATTACCTCCCTGGGCGCCATCG
TGTCTTGCTACGGCAAGACAAAGTGCACCGCCAGCAACAAGAACCGGGGCATCATC
AAGACCTTCAGCAACGGCTGCGACTACGTGAGCAACAAGGGCGTGGACACCGTTAG
CGTGGGCAACACACTGTATTACGTAAATAAACTTGAGGGCAAGAATCTGTACGTGA
AGGGCGAGCCTATCATCAACTACTACGACCCACTGGTGTTTCCATCTGATGAGTTCG
ACGCCTCCATCTCCCAGGTGAACGAGAAGATCAACCAGAGCCTGGCTTTTATCAGA
AGAAGCGATGAGCTGCTGCACAACGTGAATACCGGAAAAAGCACCACCAACATCAT
GATCACCGCCATCATTATCGTTATCATCGTGGTGCTGCTGAGTCTGATCGCCATTGG
ACTGCTGCTGTATTGCAAAGCCAAGAACACCCCCGTGACCCTGAGCAAGGACCAGC
TGAGCGGCATCAACAACATAGCTTTCTCCAAGTGACTCGAGTAAGCTGGAGCCTCGG
TGGCCATGCTTCTTGCCCCTTGGGCCTCCCCCAGCCCCTCCTCCCCTTCCTGCACCC
GTACCCCCGTGGTCTTTGAATAAAGTCTGAGTGGGCGGCAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAATGAAG
AGCATCGGATCCCGGGCCCGTCGACTGCAGAGGCCTGCATGCAAGCTTGGCGTAAT
CATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTAT
CAGCTCACTCAAAGGCGGTAATACGGTTATCACAGAATCAGGGGATAACGCAGGA
AAGAACATGTGAGCAAAAGGCCAGCAAAAGGCCAGGAACCGTAAAAAGGCCGCGT
TGCTGGCGTTTTTCCATAGGCTCCGCCCCCTGACGAGCATCACAAAAATCGACGCT
CAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTG
TGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAG
AAAAATAAACAAATAGGGGTTCCGCGCACATTTCCCCGAAAAGTGCCACCTGACGT
CTAAGAAACCATTATTATCATGACATTAACCTATAAAAATAGGCGTATCACGAGGCC
CTTTCGTC
```

5) Protein sequence of the ORF encoded in RSV mutant F A strain mRNA
SEQ ID NO: 5
MELLILKANAITTILTAVTFCFASGQNITEEFYQSTCSAVSKGYLSALRTGWYTSVITIELS
NIKKNKCNGTDAKVKLIKQELDKYKNAVTELQLLMQSTQATNNRARRELPRFMNYTLN
NAKKTNVTLSKKRKRRFLGFLLGVGSAIASGVAVCKVLHLEGEVNKIKSALLSTNKAVV
SLSNGVSVLTFKVLDLKNYIDKQLLPILNKQSCSISNIETVIEFQQKNNRLLEITREFSVNA
GVTTPVSTYMLTNSELLSLINDMPITNDQKKLMSNNVQIVRQQSYSIMCIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNVDIFNPKYDCKIMTSKTDVSSSVITSLGAIVSCYGKT KCTASNKNRGIIKTFSNGCDYVSNKGVDTVSVGNTLYYVNKQEGKSLYVKGEPIINFYD
PLVFPSDEFDASISQVNEKINQSLAFIRKSDELLHNVNAGKSTTNIMITTIIIVIIVILLSLIAV
GLLLYCKARSTPVTLSKDQLSGINNIAFSN 6) RSV mutant F A strain mRNA sequence (ORF)
SEQ ID NO: 6
AUGGAACUGCUGAUCCUGAAGGCCAACGCUAUCACAACCAUCCUCACCGCCGUGA
CAUUCUGCUUCGCCAGCGGCCAGAACAUCACCGAAGAGUUCUACCAGAGCACCUG
CUCCGCUGUGUCUAAAGGGUACCUGUCCGCCCUGAGAACCGGCUGGUAUACCAGC
GUGAUUACGAUUGAGCUGAGCAACAUCAAGAAGAACAAGUGCAACGGAACAGAC
GCCAAGGUGAAGCUGAUCAAGCAGGAGCUGGAUAAGUAUAAGAACGCCGUGACC
GAGUUGCAGCUGCUCAUGCAGUCUACACAGGCCACAAACAAUCGGGCCAGAAGAG
AGCUGCCUAGAUUCAUGAACUACACCCUGAACAACGCCAAGAAGACAAAUGUGAC
CCUGAGCAAGAAAAGAAAGCGGAGAUUCCUGGGCUUCCUGCUCGGCGUUGGCUCU
GCCAUCGCCAGCGGAGUCGCCGUGUGCAAAGUGCUGCACCUGGAAGGAGAAGUGA
ACAAGAUCAAGAGCGCCCUGCUGCUACGAACAAAGCCGUGGUGAGCCUGUCCAA
CGGCGUGAGCGUGCUGACCUUCAAGGUGCUGGACCUGAAGAACUACAUCGAUAA
GCAACUGCUGCCAAUCCUGAACAAGCAGUCUUGUAGCAUCAGCAAUAUCGAGACA
GUGAUCGAGUUCCAGCAGAAGAACAACCGGCUGCUGGAAAUCACACGGGAAUUU
AGCGUCAACGCCGGUGUGACCACCCCUGUGUCUACCUACAUGCUGACCAAUAGCG
AGCUGCUGAGCCUGAUCAAUGACAUGCCUAUUACCAACGACCAAAAGAAACUGAU
GAGCAACAAUGUACAAAUCGUUAGACAGCAGAGCUACUCCAUCAUGUGCAUCAUC
AAGGAGGAAGUGCUGGCCUACGUCGUGCAACUGCCUCUGUACGGCGUGAUCGACA
CCCCUUGUUGGAAGCUGCACACGAGCCCUCUGUGCACAACUAAUACAAAGGAAGG
CAGCAACAUCUGCCUGACCAGAACAGAUAGAGGCUGGUACUGCGACAACGCUGGA
UCUGUCAGCUUUUUCCCUCAGGCUGAAACCUGUAAAGUGCAGUCCAACCGCGUGU
UUUGCGAUACAAUGAACUCUCUGACACUGCCUAGCGAGGUGAACCUGUGUAAUG
UGGACAUCUUCAACCCCAAGUACGAUUGCAAGAUCAUGACAAGCAAGACCGAUGU
GUCUAGCAGCGUGAUUACCAGCCUGGGCGCCAUCGUGUCAUGCUACGGCAAGACC
AAGUGCACCGCCAGCAACAAAAAUCGGGGCAUCAUCAAAACCUUCAGCAACGGCU
GCGACUACGUGAGCAACAAAGGAGUGGACACCGUCUCCGUGGGCAACACCCUGUA
CUACGUGAACAAGCAGGAGGGCAAGUCUCUGUACGUGAAGGGCGAGCCAAUCAU
UAACUUCUACGACCCCCUGGUGUUCCCCUCUGAUGAGUUCGACGCCUCCAUCAGC
CAGGUGAACGAGAAGAUCAACCAGAGCCUGGCCUUCAUCAGAAAGAGCGACGAGC
UGCUGCACAACGUCAAUGCCGGCAAAAGCACCACCAACAUCAUGAUCACCACCAU
CAUCAUCGUGAUCAUUGUGAUCCUGCUGAGUCUGAUCGCUGUGGGCCUGCUGCUG
UAUUGUAAAGCUAGGUCCACCCCCGUGACACUUAGCAAGGACCAGCUGAGCGGCA
UCAACAACAUCGCAUUUAGCAAC 7) RSV mutant F A strain mRNA sequence (5'-UTR-ORF-3'UTR-Poly(A) tail)
SEQ ID NO: 7
AGGCCGGCACUCUUCUGGUCCCCACAGACUCAGAGAGAACCCGCCGCCACCAUGG
AACUGCUGAUCCUGAAGGCCAACGCUAUCACAACCAUCCUCACCGCCGUGACAUU
CUGCUUCGCCAGCGGCCAGAACAUCACCGAAGAGUUCUACCAGAGCACCUGCUCC
GCUGUGUCUAAAGGGUACCUGUCCGCCCUGAGAACCGGCUGGUAUACCAGCGUGA
UUACGAUUGAGCUGAGCAACAUCAAGAAGAACAAGUGCAACGGAACAGACGCCA
AGGUGAAGCUGAUCAAGCAGGAGCUGGAUAAGUAUAAGAACGCCGUGACCGAGU
UGCAGCUGCUCAUGCAGUCUACACAGGCCACAAACAAUCGGGCCAGAAGAGAGCU
GCCUAGAUUCAUGAACUACACCCUGAACAACGCCAAGAAGACAAAUGUGACCCUG
AGCAAGAAAAGAAAGCGGAGAUUCCUGGGCUUCCUGCUCGGCGUUGGCUCUGCCA
UCGCCAGCGGAGUCGCCGUGUGCAAAGUGCUGCACCUGGAAGGAGAAGUGAACA
AGAUCAAGAGCGCCCUGCUGUCUACGAACAAAGCCGUGGUGAGCCUGUCCAACGG
CGUGAGCGUGCUGACCUUCAAGGUGCUGGACCUGAAGAACUACAUCGAUAAGCA
ACUGCUGCCAAUCCUGAACAAGCAGUCUUGUAGCAUCAGCAAUAUCGAGACAGUG
AUCGAGUUCCAGCAGAAGAACAACCGGCUGCUGGAAAUCACACGGGAAUUUAGC
GUCAACGCCGGUGUGACCACCCCUGUGUCUACCUACAUGCUGACCAAUAGCGAGC
UGCUGAGCCUGAUCAAUGACAUGCCUAUUACCAACGACCAAAAGAAACUGAUGA
GCAACAAUGUACAAAUCGUUAGACAGCAGAGCUACUCCAUCAUGUGCAUCAUCAA
GGAGGAAGUGCUGGCCUACGUCGUGCAACUGCCUCUGUACGGCGUGAUCGACACC
CCUUGUUGGAAGCUGCACACGAGCCCUCUGUGCACAACUAAUACAAAGGAAGGCA
GCAACAUCUGCCUGACCAGAACAGAUAGAGGCUGGUACUGCGACAACGCUGGAUC
UGUCAGCUUUUUCCCUCAGGCUGAAACCUGUAAAGUGCAGUCCAACCGCGUGUUU
UGCGAUACAAUGAACUCUCUGACACUGCCUAGCGAGGUGAACCUGUGUAAUGUG
GACAUCUUCAACCCCAAGUACGAUUGCAAGAUCAUGACAAGCAAGACCGAUGUGU
CUAGCAGCGUGAUUACCAGCCUGGGCGCCAUCGUGUCAUGCUACGGCAAGACCAA
GUGCACCGCCAGCAACAAAAAUCGGGGCAUCAUCAAAACCUUCAGCAACGGCUGC
GACUACGUGAGCAACAAAGGAGUGGACACCGUCUCCGUGGGCAACACCCUGUACU
ACGUGAACAAGCAGGAGGGCAAGUCUCUGUACGUGAAGGGCGAGCCAAUCAUUA
ACUUCUACGACCCCCUGGUGUUCCCCUCUGAUGAGUUCGACGCCUCCAUCAGCCA
GGUGAACGAGAAGAUCAACCAGAGCCUGGCCUUCAUCAGAAAGAGCGACGAGCU
GCUGCACAACGUCAAUGCCGGCAAAAGCACCACCAACAUCAUGAUCACCACCAUC
AUCAUCGUGAUCAUUGUGAUCCUGCUGAGUCUGAUCGCUGUGGGCCUGCUGCUG
UAUUGUAAAGCUAGGUCCACCCCCGUGACACUUAGCAAGGACCAGCUGAGCGGCA
UCAACAACAUCGCAUUUAGCAACUGAUAAAGCUGGAGCCUCGGUGGCCUUGCUUC
UUGCCCCUUGGGCCUCCCCCCAGCCCCUCCUCCCCCUUCCUGCACCCGUACCCCCGU
GGUCUUUGAAUAAAGUCUGAGUGGGCGGCAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAAAAAAAAAAAAAAAAAA 8) Sequence of pUC57 plasmid encoding RSV mutant F A strain mRNA (RSV mutant F A strain mRNA sequence has been underlined)
SEQ ID NO: 8

```
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGTC
AGCGGGTGTTGGCGGGTGTCGGGGCTGGCTTAACTATGCGGCATCAGAGCAGATTG
TACTGAGAGTGCACCATATGCGGTGTGAAATACCGCACAGATGCGTAAGGAGAAAA
TACCGCATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GAGAATTCGAGCTCGGTACCTCGCGAATACATCTAGATTAATACGACTCACTATAAG
GCCGGCACTCTTCTGGTCCCCACAGACTCAGAGAGAACCCGCCGCCACCATGGAAC
TGCTGATCCTGAAGGCCAACGCTATCACAACCATCCTCACCGCCGTGACATTCTGCT
TCGCCAGCGGCCAGAACATCACCGAAGAGTTCTACCAGAGCACCTGCTCCGCTGTGT
CTAAAGGGTACCTGTCCGCCCTGAGAACCGGCTGGTATACCAGCGTGATTACGATTG
AGCTGAGCAACATCAAGAAGAACAAGTGCAACGGAACAGACGCCAAGGTGAAGCT
GATCAAGCAGGAGCTGGATAAGTATAAGAACGCCGTGACCGAGTTGCAGCTGCTCA
TGCAGTCTACACAGGCCACAAACAATCGGGCCAGAAGAGAGCTGCCTAGATTCATG
AACTACACCCTGAACAACGCCAAGAAGACAAATGTGACCCTGAGCAAGAAAAGAA
AGCGGAGATTCCTGGGCTTCCTGCTCGGCGTTGGCTCTGCCATCGCCAGCGGAGTCG
CCGTGTGCAAAGTGCTGCACCTGGAAGGAGAAGTGAACAAGATCAAGAGCGCCCTG
CTGTCTACGAACAAAGCCGTGGTGAGCCTGTCCAACGGCGTGAGCGTGCTGACCTTC
AAGGTGCTGGACCTGAAGAACTACATCGATAAGCAACTGCTGCCAATCCTGAACAA
GCAGTCTTGTAGCATCAGCAATATCGAGACAGTGATCGAGTTCCAGCAGAAGAACA
ACCGGCTGCTGGAAATCACACGGGAATTTAGCGTCAACGCCGGTGTGACCACCCCT
GTGTCTACCTACATGCTGACCAATAGCGAGCTGCTGAGCCTGATCAATGACATGCCT
ATTACCAACGACCAAAAGAAACTGATGAGCAACAATGTACAAATCGTTAGACAGCA
GAGCTACTCCATCATGTGCATCATCAAGGAGGAAGTGCTGGCCTACGTCGTGCAACT
GCCTCTGTACGGCGTGATCGACACCCCTTGTTGGAAGCTGCACACGAGCCCTCTGTG
CACAACTAATACAAAGGAAGGCAGCAACATCTGCCTGACCAGAACAGATAGAGGCT
GGTACTGCGACAACGCTGGATCTGTCAGCTTTTTCCCTCAGGCTGAAACCTGTAAAG
TGCAGTCCAACCGCGTGTTTTGCGATACAATGAACTCTCTGACACTGCCTAGCGAGG
TGAACCTGTGTAATGTGGACATCTTCAACCCCAAGTACGATTGCAAGATCATGACAA
GCAAGACCGATGTGTCTAGCAGCGTGATTACCAGCCTGGGCGCCATCGTGTCATGCT
ACGGCAAGACCAAGTGCACCGCCAGCAACAAAAATCGGGGCATCATCAAAACCTTC
AGCAACGGCTGCGACTACGTGAGCAACAAAGGAGTGGACACCGTCTCCGTGGGCAA
CACCCTGTACTACGTGAACAAGCAGGAGGGCAAGTCTCTGTACGTGAAGGGCGAGC
CAATCATTAACTTCTACGACCCCCTGGTGTTCCCCTCTGATGAGTTCGACGCCTCCAT
CAGCCAGGTGAACGAGAAGATCAACCAGAGCCTGGCCTTCATCAGAAAGAGCGACG
AGCTGCTGCACAACGTCAATGCCGGCAAAAGCACCACCAACATCATGATCACCACC
ATCATCATCGTGATCATTGTGATCCTGCTGAGTCTGATCGCTGTGGGCCTGCTGCTGT
ATTGTAAAGCTAGGTCCACCCCCGTGACACTTAGCAAGGACCAGCTGAGCGGCATC
AACAACATCGCATTTAGCAACTGATAAAGCTGGAGCTCGGTGGCCTTGCTTCTTGC
CCCTTGGGCCTCCCCCCAGCCCCTCCTCCCCTTCCTGCACCCGTACCCCCGTGGTCTT
TGAATAAAGTCTGAGTGGGCGGCAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAGGGCCCGTTTAAACATCGGAT
CCCCGGGCCCGTCGACTGCAGAGGCCTGCATGCAAGCTTGGTGTAATCATGGTCATAG
CTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAGCTCACTC
AAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATC
TTCACCTAGATCCTTTTAAATTAAAAATGAAGTTTTAAATCAAGCCCAATCTGAATA
ATGTTACAACCAATTAACCAATTCTGATTAGAAAAACTCATCGAGCATCAAATGAAA
CTGCAATTTATTCATATCAGGATTATCAATACCATATTTTTGAAAAAGCCGTTTCTGT
AATGAAGGAGAAAACTCACCGAGGCAGTTCCATAGGATGGCAAGATCCTGGTATCG
GTCTGCGATTCCGACTCGTCCAACATCAATACAACCTATTAATTTCCCCTCGTCAAA
AATAAGGTTATCAAGTGAGAAATCACCATGAGTGACGACTGAATCCGGTGAGAATG
GCAAAAGTTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCGAG
ACGAAATACGCGATCGCTGTTAAAAGGACAATTACAAACAGGAATCGAATGCAACC
GGCGCAGGAACACTGCCAGCGCATCAACAATATTTTCACCTGAATCAGGATATTCTT
CTAATACCTGGAATGCTGTTTTTCCGGGGATCGCAGTGGTGAGTAACCATGCATCAT
CAGGAGTACGGATAAAATGCTTGATGGTCGGAAGAGGCATAAATTCCGTCAGCCAG
```

-continued

TTTAGTCTGACCATCTCATCTGTAACATCATTGGCAACGCTACCTTTGCCATGTTTCA
GAAACAACTCTGGCGCATCGGGCTTCCCATACAAGCGATAGATTGTCGCACCTGATT
GCCCGACATTATCGCGAGCCCATTTATACCCATATAAATCAGCATCCATGTTGGAAT
TTAATCGCGGCCTCGACGTTTCCCGTTGAATATGGCTCATAACACCCCTTGTATTACT
GTTTATGTAAGCAGACAGTTTTATTGTTCATGATGATATATTTTTATCTTGTGCAATG
TAACATCAGAGATTTTGAGACACGGGCCAGAGCTGCA

9) Protein sequence of the ORF encoded in hMPV-F mRNA
SEQ ID NO: 9
MSWKVVIIFSLLITPQHGLKESYLEESCSTITEGYLSVLRTGWYTNVFTLEVGDVENLTC
ADGPSLIKTELDLTKSALRELKTVSADQLAREEQIENPRQSRFVLGAIALGVATAAAVTA
GVAIAKTIRLESEVTAIKNALKKTNEAVSTLGNGVRVLATAVRELKDFVSKNLTRAINK
NKCDIDDLKMAVSFSQFNRRFLNVVRQFSDNAGITPAISLDLMTDAELARAVSNMPTSA
GQIKLMLENRAMVRRKGFGILIGVYGSSVIYMVOLPIFGVIDTPCWIVKAAPSCSEKKGN
YACLLREDQGWYCQNAGSTVYYPNEKDCETRGDHVFCDTAAGINVAEQSKECNINIST
TNYPCKVSTGRHPISMVALSPLGALVACYKGVSCSIGSNRVGIIKQLNKGCSYITNQDAD
TVTIDNTVYQLSKVEGEQHVIKGRPVSSSFDPVKFPEDQFNVALDQVFENIENSQALVDQ
SNRILSSAEKGNTGFIIVIILIAVLGSSMILVSICIIIKKTKKPTGAPPELSGVTNNGFIPHS 10) hMPV-F mRNA (ORF)
SEQ ID NO: 10
AUGAGCUGGAAGGUGGUGAUCAUCUUCAGCCUGCUGAUCACCCCUCAGCACGGCC
UGAAAGAGAGCUACCUGGAAGAAAGCUGCUCUACCAUCACAGAGGGCUACCUGA
GUGUGCUGCGGACCGGCUGGUACACAAACGUGUUUACCCUGGAAGUGGGCGACG
UGGAAAACCUGACAUGCGCCGAUGGCCCCAGCCUGAUUAAGACAGAGCUGGACCU
GACAAAGAGCGCCCUGAGAGAACUGAAGACAGUCAGCGCUGAUCAACUGGCCAGG
GAGGAGCAGAUCGAGAACCCCAGACAGUCCAGAUUCGUGCUCGGUGCCAUCGCCC
UGGGCGUGGCGACAGCUGCCGCUGUUACCGCUGGCGUGGCUAUCGCCAAGACCAU
CAGACUGGAAUCUGAGGUGACCGCCAUCAAGAAUGCCCUGAAGAAGACCAAUGA
GGCCGUGUCUACACUGGGAAAUGGCGUGCGGGUGCUGGCUACAGCCGUCCGGGAA
CUGAAAGACUUCGUGUCCAAGAACUUGACCAGAGCCAUCAACAAGAACAAGUGCG
AUAUCGACGACCUGAAGAUGGCCGUGAGCUUCAGCCAGUUCAACCGGCGGUUCCU
GAACGUUGUGCGGCAGUUUAGCGACAACGCCGGAAUCACCCCAGCCAUCAGCCUG
GACCUGAUGACCGACGCCGAGCUGGCCAGAGCCGUGAGCAACAUGCCUACAAGCG
CCGGCCAGAUCAAGCUGAUGCUGGAGAAUCGGGCCAUGGUGAGAAGAAAGGGCU
UUGGCAUCCUGAUCGGCGUGUACGGCAGCAGCGUGAUCUACAUGGUGCAGCUGCC
UAUCUUCGGCGUGAUCGAUACCCCUUGCUGGAUCGUGAAGGCCGCCCCUAGCUGU
AGCGAGAAAAAGGGAAACUACGCCUGUCUGCUGAGAGAAGAUCAGGGCUGGUAU
UGCCAGAACGCCGGCAGCACCGUGUACUACCCCAACGAGAAGGACUGCGAGACAA
GAGGCGAUCACGUGUUCUGCGACACCGCCGCCGGCAUCAACGUUGCUGAGCAAAG
CAAGGAAUGCAACAUCAACAUCAGCACCACCAACUACCCUUGUAAAGUGAGCACC
GGAAGACACCCCAUCUCCAUGGUCGCACUCUCCCCUCUGGGCGCCCUGGUCGCCU
GCUACAAGGGCGUGUCUUGUAGCAUCGGAAGCAACCGCGUUGGCAUCAUCAAGCA
GCUGAACAAAGGAUGUUCUUAUAUCACCAACCAGGAUGCCGACACCGUGACAAUC
GACAAUACCGUCUACCAGCUGAGCAAGGUGGAAGGCGAGCAGCACGUGAUUAAG
GGCAGACCUGUGUCCUCUAGCUUCGACCCCGUGAAGUUCCCCGAGGACCAGUUCA
AUGUGGCCCUGGAUCAAGUGUUUGAGAACAUCGAGAACAGCCAGGCCCUGGUGG
ACCAGAGCAAUAGAAUCCUGUCCUCCGCUGAGAAAGGCAACACCGGCUUCAUCAU
CGUGAUCAUCCUGAUCGCCGUGCUGGGCUCUAGCAUGAUCCUGGUGUCUAUCUGC
AUUAUUAUCAAGAAAACCAAGAAGCCUACCGGCGCUCCACCUGAGCUGAGCGGAG
UGACCAACAACGGCUUCAUCCCUCAUUCU 11) hMPV-F mRNA sequence (5'-UTR-ORF-3'UTR-Poly(A) tail)
SEQ ID NO: 11
AGGCCGGCACUCUUCUGGUCCCCACAGACUCAGAGAGAACCCGCCGCCACCAUGA
GCUGGAAGGUGGUGAUCAUCUUCAGCCUGCUGAUCACCCCUCAGCACGGCCUGAA
AGAGAGCUACCUGGAAGAAAGCUGCUCUACCAUCACAGAGGGCUACCUGAGUGU
GCUGCGGACCGGCUGGUACACAAACGUGUUUACCCUGGAAGUGGGCGACGUGGA
AAACCUGACAUGCGCCGAUGGCCCCAGCCUGAUUAAGACAGAGCUGGACCUGACA
AAGAGCGCCCUGAGAGAACUGAAGACAGUCAGCGCUGAUCAACUGGCCAGGGAG
GAGCAGAUCGAGAACCCCAGACAGUCCAGAUUCGUGCUCGGUGCCAUCGCCCUGG
GCGUGGCGACAGCUGCCGCUGUUACCGCUGGCGUGGCUAUCGCCAAGACCAUCAG
ACUGGAAUCUGAGGUGACCGCCAUCAAGAAUGCCCUGAAGAAGACCAAUGAGGCC
GUGUCUACACUGGGAAAUGGCGUGCGGGUGCUGGCUACAGCCGUCCGGGAACUG
AAAGACUUCGUGUCCAAGAACUUGACCAGAGCCAUCAACAAGAACAAGUGCGAU
AUCGACGACCUGAAGAUGGCCGUGAGCUUCAGCCAGUUCAACCGGCGGUUCCUGA
ACGUUGUGCGGCAGUUUAGCGACAACGCCGGAAUCACCCCAGCCAUCAGCCUGGA
CCUGAUGACCGACGCCGAGCUGGCCAGAGCCGUGAGCAACAUGCCUACAAGCGCC
GGCCAGAUCAAGCUGAUGCUGGAGAAUCGGGCCAUGGUGAGAAGAAAGGGCUUU
GGCAUCCUGAUCGGCGUGUACGGCAGCAGCGUGAUCUACAUGGUGCAGCUGCCUA
UCUUCGGCGUGAUCGAUACCCCUUGCUGGAUCGUGAAGGCCGCCCCUAGCUGUAG
CGAGAAAAAGGGAAACUACGCCUGUCUGCUGAGAGAAGAUCAGGGCUGGUAUUG
CCAGAACGCCGGCAGCACCGUGUACUACCCCAACGAGAAGGACUGCGAGACAAGA
GGCGAUCACGUGUUCUGCGACACCGCCGCCGGCAUCAACGUUGCUGAGCAAAGCA
AGGAAUGCAACAUCAACAUCAGCACCACCAACUACCCUUGUAAAGUGAGCACCGG
AAGACACCCCAUCUCCAUGGUCGCACUCUCCCCUCUGGGCGCCCUGGUCGCCUGC
UACAAGGGCGUGUCUUGUAGCAUCGGAAGCAACCGCGUUGGCAUCAUCAAGCAGC
UGAACAAAGGAUGUUCUUAUAUCACCAACCAGGAUGCCGACACCGUGACAAUCGA
CAAUACCGUCUACCAGCUGAGCAAGGUGGAAGGCGAGCAGCACGUGAUUAAGGG -continued

```
CAGACCUGUGUCCUCUAGCUUCGACCCCGUGAAGUUCCCCGAGGACCAGUUCAAU
GUGGCCCUGGAUCAAGUGUUUGAGAACAUCGAGAACAGCCAGGCCCUGGUGGACC
AGAGCAAUAGAAUCCUGUCCUCCGCUGAGAAAGGCAACACCGGCUUCAUCAUCGU
GAUCAUCCUGAUCGCCGUGCUGGGCUCUAGCAUGAUCCUGGUGUCUAUCUGCAUU
AUUAUCAAGAAAACCAAGAAGCCUACCGGCGCUCCACCUGAGCUGAGCGGAGUGA
CCAACAACGGCUUCAUCCCUCAUUCUUGACUCGAGUAAGCUGGAGCCUCGGUGGC
CAUGCUUCUUGCCCCUUGGGCCUCCCCCCAGCCCCUCCUCCCCUUCCUGCACCCGU
ACCCCCGUGGUCUUUGAAUAAAGUCUGAGUGGGCGGCAAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAA
```

12) Sequence of pUC57 plasmid encoding hMPV-F mRNA (hMPV-F mRNA sequence has been underlined)

SEQ ID NO: 12

```
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGTC
AGCGGGTGTTGGCGGGTGTCGGGGCTGGCTTAACTATGCGGCATCAGAGCAGATTG
TACTGAGAGTGCACCATATGCGGTGTGAAATACCGCACAGATGCGTAAGGAGAAAA
TACCGCATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GAGAATTCGAGCTCGGTACCTCGCGAATACATCTAGATTAATACGACTCACTATAAG
GCCGGCACTCTTCTGGTCCCCACAGACTCAGAGAGAACCCGCCGCCACCATGAGCT
GGAAGGTGGTGATCATCTTCAGCCTGCTGATCACCCCTCAGCACGGCCTGAAAGAG
AGCTACCTGGAAGAAAGCTGCTCTACCATCACAGAGGGCTACCTGAGTGTGCTGCG
GACCGGCTGGTACACAAACGTGTTTACCCTGGAAGTGGGCGACGTGGAAAACCTGA
CATGCGCCGATGGCCCCAGCCTGATTAAGACAGAGCTGGACCTGACAAAGAGCGCC
CTGAGAGAACTGAAGACAGTCAGCGCTGATCAACTGGCCAGGGAGGAGCAGATCGA
GAACCCCAGACAGTCCAGATTCGTGCTCGGTGCCATCGCCCTGGGCGTGGCGACAG
CTGCCGCTGTTACCGCTGGCGTGGCTATCGCCAAGACCATCAGACTGGAATCTGAGG
TGACCGCCATCAAGAATGCCCTGAAGAAGACCAATGAGGCCGTGTCTACACTGGGA
AATGGCGTGCGGGTGCTGGCTACAGCCGTCCGGGAACTGAAAGACTTCGTGTCCAA
GAACTTGACCAGAGCCATCAACAAGAACAAGTGCGATATCGACGACCTGAAGATGG
CCGTGAGCTTCAGCCAGTTCAACCGGCGGTTCCTGAACGTTGTGCGGCAGTTTAGCG
ACAACGCCGGAATCACCCCAGCCATCAGCCTGGACCTGATGACCGACGCCGAGCTG
GCCAGAGCCGTGAGCAACATGCCTACAAGCGCCGGCCAGATCAAGCTGATGCTGGA
GAATCGGGCCATGGTGAGAAGAAAGGGCTTTGGCATCCTGATCGGCGTGTACGGCA
GCAGCGTGATCTACATGGTGCAGCTGCCTATCTTCGGCGTGATCGATACCCCTTGCT
GGATCGTGAAGGCCGCCCCTAGCTGTAGCGAGAAAAAGGGAAACTACGCCTGTCTG
CTGAGAGAAGATCAGGGCTGGTATTGCCAGAACGCCGGCAGCACCGTGTACTACCC
CAACGAGAAGGACTGCGAGACAAGAGGCGATCACGTGTTCTGCGACACCGCCGCCG
GCATCAACGTTGCTGAGCAAAGCAAGGAATGCAACATCAACATCAGCACCACCAAC
TACCCTTGTAAAGTGAGCACCGGAAGACACCCCATCTCCATGGTCGCACTCTCCCCT
CTGGGCGCCCTGGTCGCCTGCTACAAGGGCGTGTCTTGTAGCATCGGAAGCAACCGC
GTTGGCATCATCAAGCAGCTGAACAAAGGATGTTCTTATATCACCAACCAGGATGCC
GACACCGTGACAATCGACAATACCGTCTACCAGCTGAGCAAGGTGGAAGGCGAGCA
GCACGTGATTAAGGGCAGACCTGTGTCCTCTAGCTTCGACCCCGTGAAGTTCCCCGA
GGACCAGTTCAATGTGGCCCTGGATCAAGTGTTTGAGAACATCGAGAACAGCCAGG
CCCTGGTGGACCAGAGCAATAGAATCCTGTCCTCCGCTGAGAAAGGCAACACCGGC
TTCATCATCGTGATCATCCTGATCGCCGTGCTGGGCTCTAGCATGATCCTGGTGTCTA
TCTGCATTATTATCAAGAAAACCAAGAAGCCTACCGGCGCTCCACCTGAGCTGAGC
GGAGTGACCAACAACGGCTTCATCCCTCATTCTTGACTCGAGTAAGCTGGAGCCTCG
GTGGCCATGCTTCTTGCCCCTTGGGCCTCCCCCCAGCCCCTCCTCCCCTTCCTGCACC
CGTACCCCCGTGGTCTTTGAATAAAGTCTGAGTGGGCGGCAAAAAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAATGAA
GAGCATCGGATCCCGGGCCCGTCGACTGCAGAGGCCTGCATGCAAGCTTGGTGTAA
TCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGC
TCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAAGCCC
AATCTGAATAATGTTACAACCAATTAACCAATTCTGATTAGAAAAACTCATCGAGCA
TCAAATGAAACTGCAATTTATTCATATCAGGATTATCAATACCATATTTTTGAAAAA
```

```
GCCGTTTCTGTAATGAAGGAGAAAACTCACCGAGGCAGTTCCATAGGATGGCAAGA
TCCTGGTATCGGTCTGCGATTCCGACTCGTCAACATCAATACAACCTATTAATTTCC
CCTCGTCAAAAATAAGGTTATCAAGTGAGAAATCACCATGAGTGACGACTGAATCC
GGTGAGAATGGCAAAAGTTTATGCATTTCTTTCCAGACTTGTTCAACAGGCCAGCCA
TTACGCTCGTCATCAAAATCACTCGCATCAACCAAACCGTTATTCATTCGTGATTGC
GCCTGAGCGAGACGAAATACGCGATCGCTGTTAAAAGGACAATTACAAACAGGAAT
CGAATGCAACCGGCGCAGGAACACTGCCAGCGCATCAACAATATTTTCACCTGAAT
CAGGATATTCTTCTAATACCTGGAATGCTGTTTTTCCGGGGATCGCAGTGGTGAGTA
ACCATGCATCATCAGGAGTACGGATAAAATGCTTGATGGTCGGAAGAGGCATAAAT
TCCGTCAGCCAGTTTAGTCTGACCATCTCATCTGTAACATCATTGGCAACGCTACCTT
TGCCATGTTTCAGAAACAACTCTGGCGCATCGGGCTTCCCATACAAGCGATAGATTG
TCGCACCTGATTGCCCGACATTATCGCGAGCCCATTTATACCCATATAAATCAGCAT
CCATGTTGGAATTTAATCGCGGCCTCGACGTTTCCCGTTGAATATGGCTCATAACAC
CCCTTGTATTACTGTTTATGTAAGCAGACAGTTTTATTGTTCATGATGATATATTTTT
ATCTTGTGCAATGTAACATCAGAGATTTTGAGACACGGGCCAGAGCTGCA
```

EXAMPLES

Example 1—DNA Templates Used for In Vitro Transcription and Protein Expression of RSV F Genes DNA constructs used for RSV mutant F B strain mRNA productions (in vitro transcription, IVT) consist of 1) T7 promoter, 2) 5' untranslated region (UTR), 3) open reading frame (ORF) of (RSV mutant F B strain) modified from human RSV strain B membrane glycoprotein DNA (GenBank: MZ515553.1), 4) 3'UTR, and 5) 120 bases of poly adenine (polyA). 5'UTR and 3'UTR sequences were from human hemoglobin subunit alpha 1 (HBA1) mRNA (GenBank: NM_000558.5). The sequence of pUC57 plasmid encoding RSV mutant F B strain mRNA is shown in SEQ ID NO: 4.

The DNA fragment was synthesized and subcloned into pUC57-Kan vector by GenScript (Piscataway, NJ: www-.genscript.com/vector/SD1176-pUC57_plasmid_DNA.html). For a stabilized prefusion form of RSV-F protein, a mutant RSV-F (Fmut) with four amino acid substitutions (S155C, S190F, V207L, and S290C), was generated from a mutagenesis on the RSV-F clone by GenScript (FIG. 1 top).

DNA construct used for RSV mutant F A strain mRNA productions (in vitro transcription, IVT) consist of 1) T7 promoter, 2) 5' untranslated region (UTR), 3) open reading frame (ORF) of RSV mutant F A strain modified from human RSV strain A2 membrane glycoprotein DNA (GenBank: KT992094.1), 4) 3'UTR, and 5) 120 bases of poly adenine (polyA). 5'UTR and 3'UTR sequences are from human hemoglobin subunit alpha 1 (HBA1) mRNA (GenBank: NM_000558.5). The sequence of pUC57 plasmid encoding RSV mutant F A strain is shown in SEQ ID NO: 8.

The DNA fragment was synthesized and subcloned into pUC57-Kan vector by GenScript (Piscataway, NJ: www-.genscript.com/vector/SD1176-pUC57_plasmid_DNA.html). For a stabilized prefusion form of RSV-F protein, a mutant RSV-F (Fmut) with four amino acid substitutions (S155C, S190F, V207L, and S290C), was generated from a mutagenesis on the RSV-F clone by GenScript.

Example 2—In Vitro Transcription (IVT)

The plasmid vector was linearized by restriction enzyme, PmeI or SapI (New England Biolabs) for RSV F IVTs. N1-Methylpseudouridine (m1Ψ) was purchased from BOC Sciences (Shirley, NY). IVT condition was followed by manufacture's recommendation (TranscriptAid T7 High Yield Transcription Kit, ThermoFisher) as below:
- ATP/CTP/GTP/m1ψTP: 5 mM each
- SmartCap (SC101, ST Pharm): 4 mM
- Linear template DNA: 1 ug of plasmid or 0.5 ug of PCR product
- T7 RNA polymerase enzyme mix: 2 ul IVT was carried out in 20 ul reaction incubated at 37° ° C. for 2 hours. The template DNA was removed by 2 units of DNase I (ThermoFisher) to be treated at 37° C. for 15 min followed by a column purification (Monarch RNA Cleanup Kit, New England Biolabs).

The IVT product of RSV mutant F B strain gene and the IVT product of RSV mutant F A strain gene were analyzed by agarose gel, and their 2knt long mRNA products were detected. Here, after IVTs from DNA templates of RSV mutant F B strain and RSV mutant F A strain mRNAs, 100 ng of mRNA was run on 1% agarose of E-GEL EX in E-Gel Power Snap Electrophoresis Device (ThermoFisher) shown in FIG. 1 bottom.

Example 3—Transfection and Western Blots 1 ug of each mRNAs were transfected into 293FT cells or SJCRH30 (CRL-2061, ATCC) in 12 well plate using Lipofectamine MesseangerMax, 2 or 4 ul at 1:2 ratio (ThermoFisher) according to the manufacturer's protocol. Cell lysate was prepared in NP-40 lysis buffer (150 mM sodium chloride/1% NP-40/50 mM Tris pH8.0) after 24 hours of transfection.

Mouse monoclonal anti-RSV-F antibody (NB110-37246, Noivus Biologicals) was used for Western Blot. Detection of protein was using a HRP-conjugated goat anti-mouse IgG antibody (115-035-062, Jackson ImmunoResearch) and SuperSignal West Pico Plus Chemiluminescent Substrate (ThermoScientific).

Figure 2:
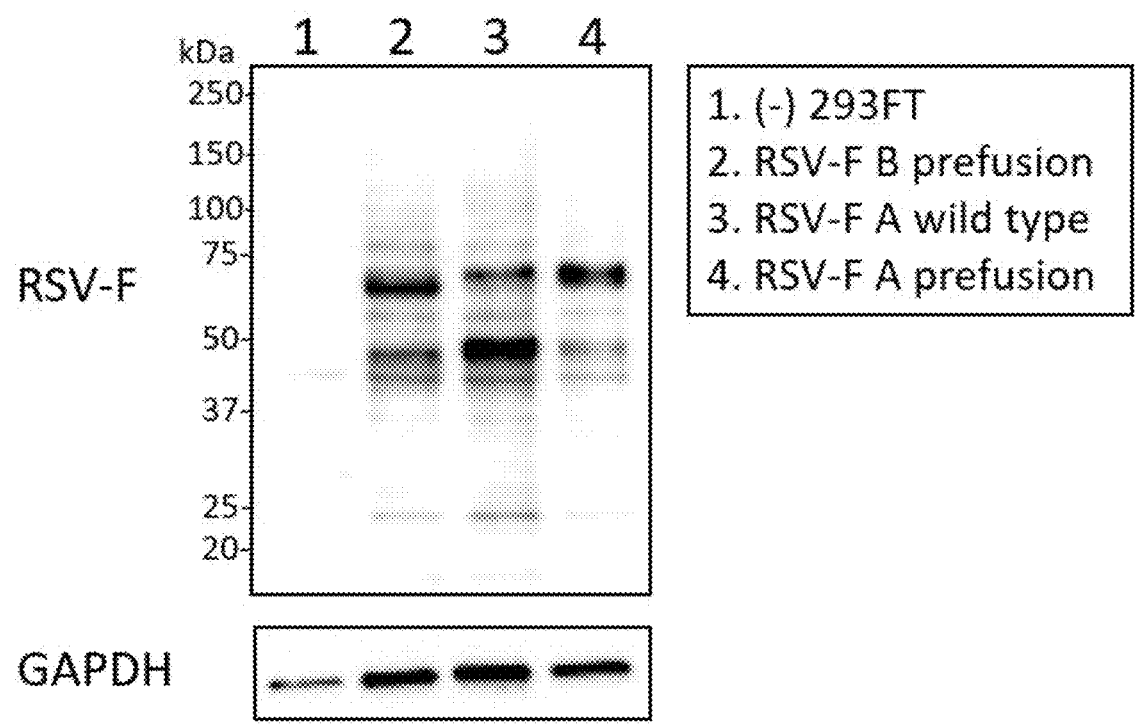
FIG. 2 shows the results of RSV-F western blot.

The expression of RSV mutant F proteins were detected in the transfected 293 FT cells with individual mRNAs (FIG. 2). Here, 1 ug RSV mRNAs were individually transfected into 293FT cells. The cell lysates were subjected to Western Blot, and (RSV mutant F from B and A strains)(lane 2 and 4) were detected as shown in FIG. 2. Lanes 1: negative control.

Example 4—Immunogenicity Study for RSV Vaccine Composition

This study was designed to test the immunogenicity in mice of the RSV vaccine composition of the present disclosure.

Figure 3:
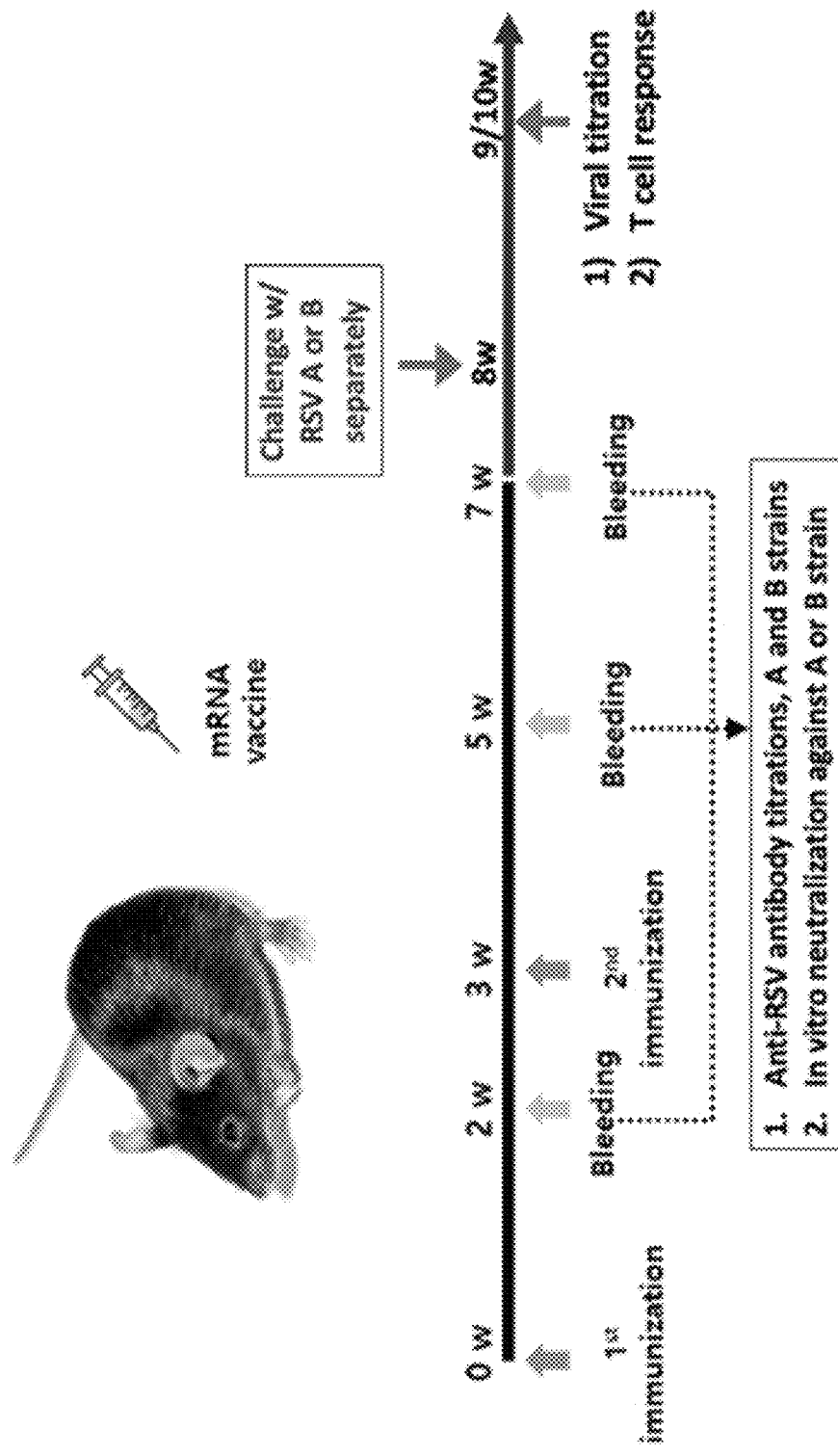
FIG. 3 describes the schedule of immunogenicity and challenge test of the combined of RSV mutant F A strain mRNA vaccine and RSV mutant F B strain mRNA vaccine in mice.
Figure 4:
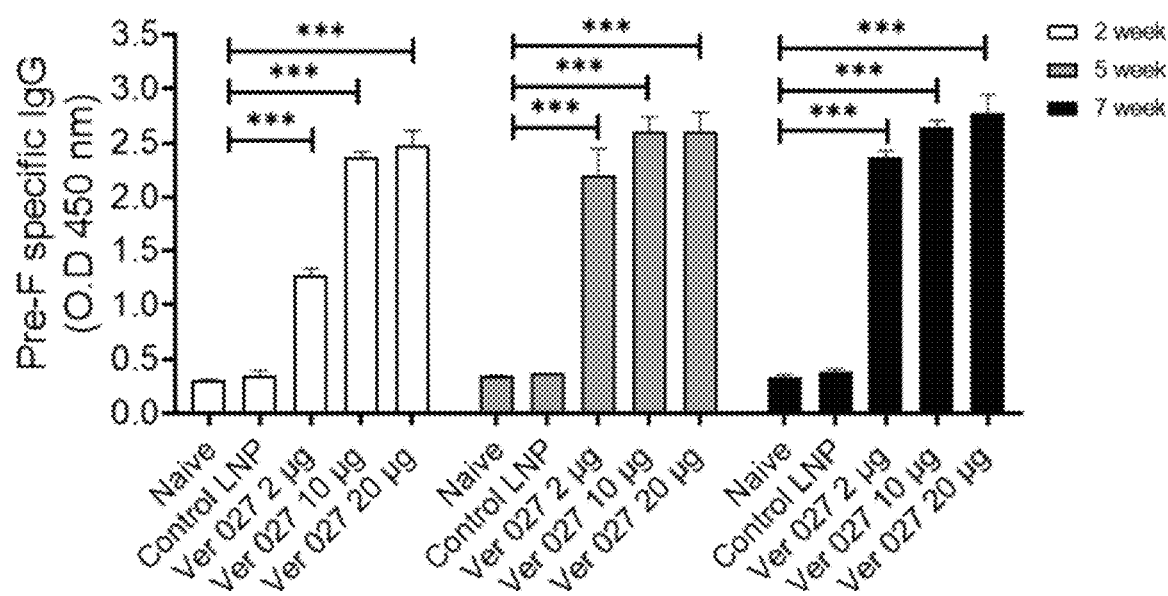
FIG. 4 shows the results of RSV pre-fusion specific IgG immunogenic responses. Ver 027 is the combined of RSV mutant F A strain mRNA vaccine and RSV mutant F B strain mRNA vaccine.
Figure 5:
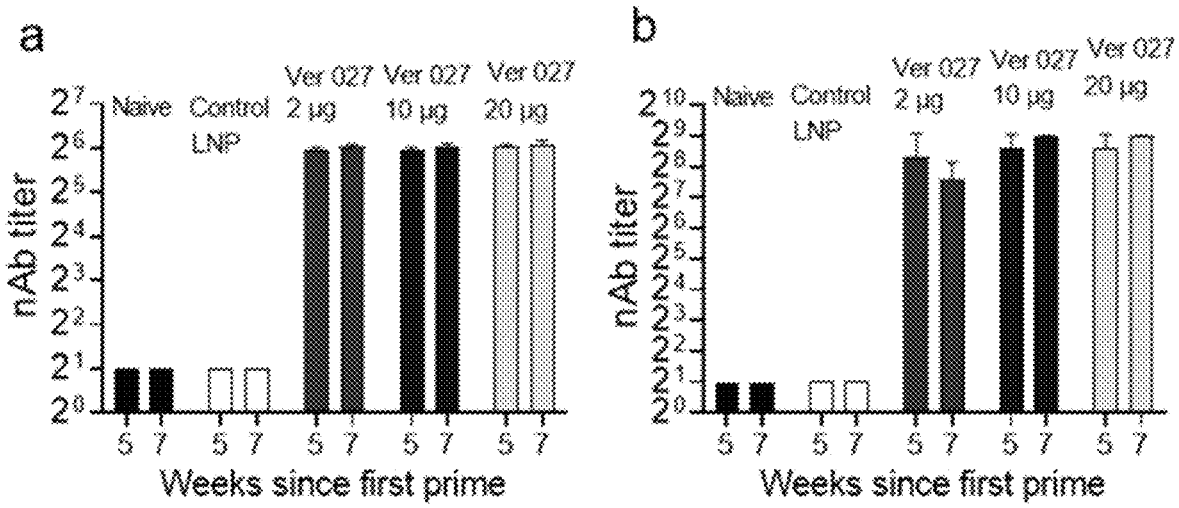
FIG. 5 shows neutralizing antibody (nAb) titration to RSV mutant F A strain (a of FIG. 3) and RSV mutant F B strain (b of FIG. 3) strains.
Figure 6:
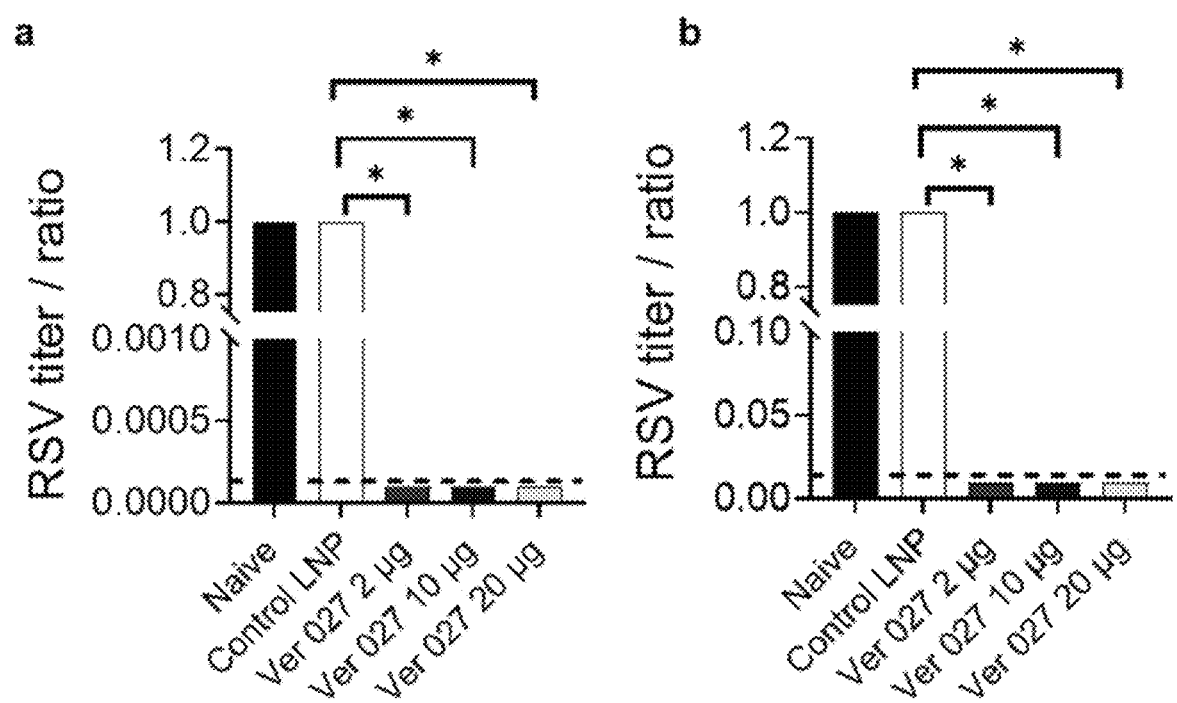
FIG. 6 shows lung viral loads after the combined of RSV mutant F A strain mRNA vaccine and RSV mutant F B strain mRNA vaccine challenge.

Mice were immunized intramuscularly (IM) with the RSV vaccine composition of the present disclosure (RSV mutant F B strain, and RSV mutant F A strain). The vaccine composition of the present disclosure was chemically modified or unmodified. A total of two immunizations are given at 3-week intervals (i.e., at weeks 0 and 3), and sera were collected after each immunization until weeks 7 (weeks 2, 5 and 7) (FIG. 3). Serum IgG titers specific to Pre-F protein in the sera collected at weeks 2, 5, and 7, were determined by ELISA (FIG. 4). The neutralization titers of the pooled sera from weeks 2, 5 and 7 against RSV A and B strains were separately determined by plaque assay-based neutralization assay (FIG. 5). To detect the T cell response of RSV vaccine in the vaccinated mice, the spleens in the immunized and RSV challenged (4 days) mice were harvested and stained with RSV F85-93 tetramer (FIG. 6). % of CD8+ T cells stained with F85-93 tetramer were determined by flow cytometric analysis (FIG. 6).

Example 5—Virus Challenge Study for RSV Vaccine Composition

Figure 7:
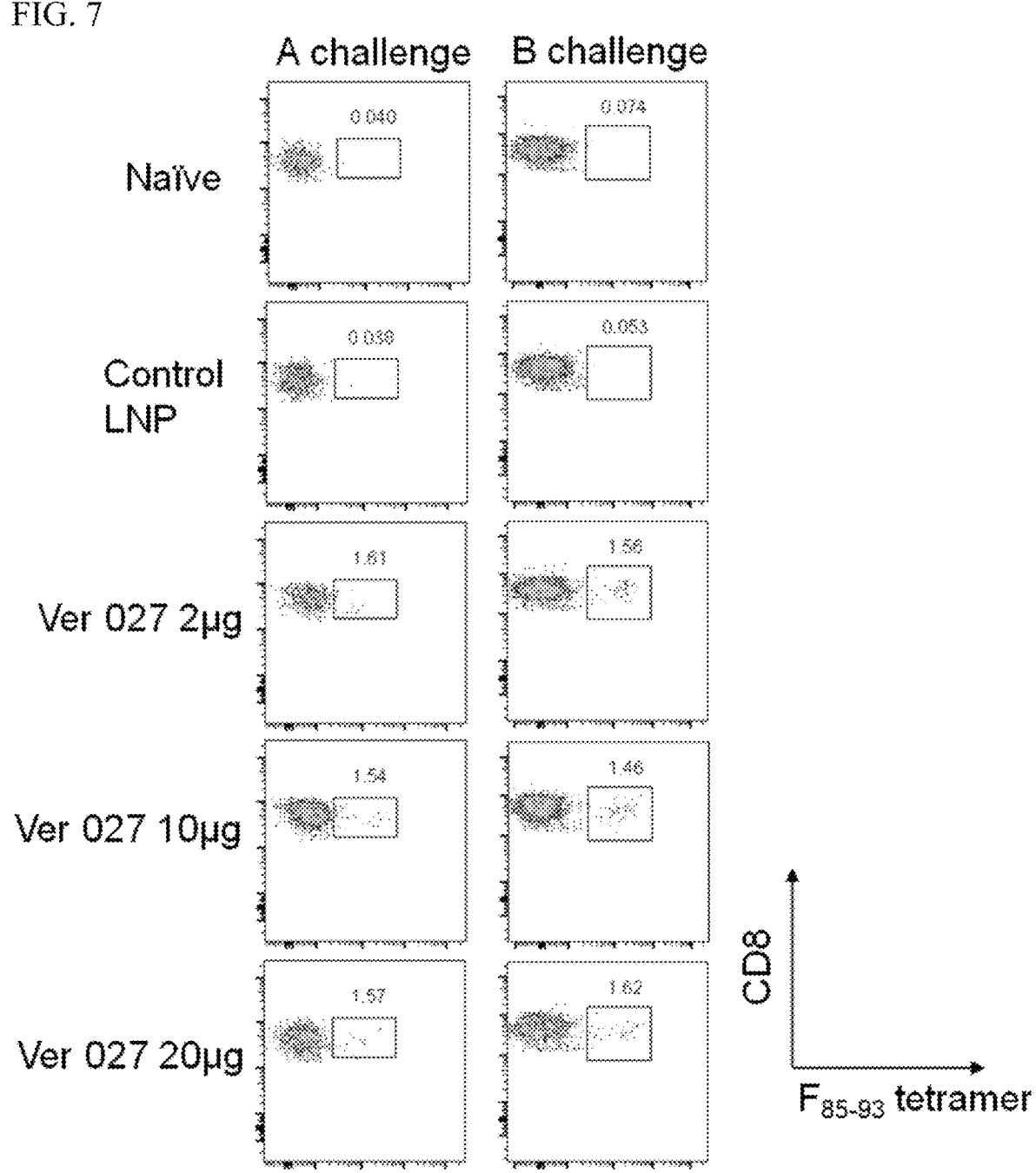
FIG. 7 shows direct enumeration of F85-93 epitope-specific CD8+T lymphocytes.

This study was designed to evaluate the protection efficacy of the RSV vaccine against RSV subtype A and subtype B infection in mice post immunization with the proper doses and formulations described in the Immunogenicity study. The mice immunized twice at weeks of 0 and 3 were divided into two groups, and each group was separately infected by RSV A2 strain or RSV B1 strain at week 8. In vivo lung viral titers were monitored at days 4 post infection. Viral titers isolated from the collected lungs were determined by plaque assay for RSV A2 and Q-RT-PCR for RSV B1 (FIG. 7).

Figure 8:
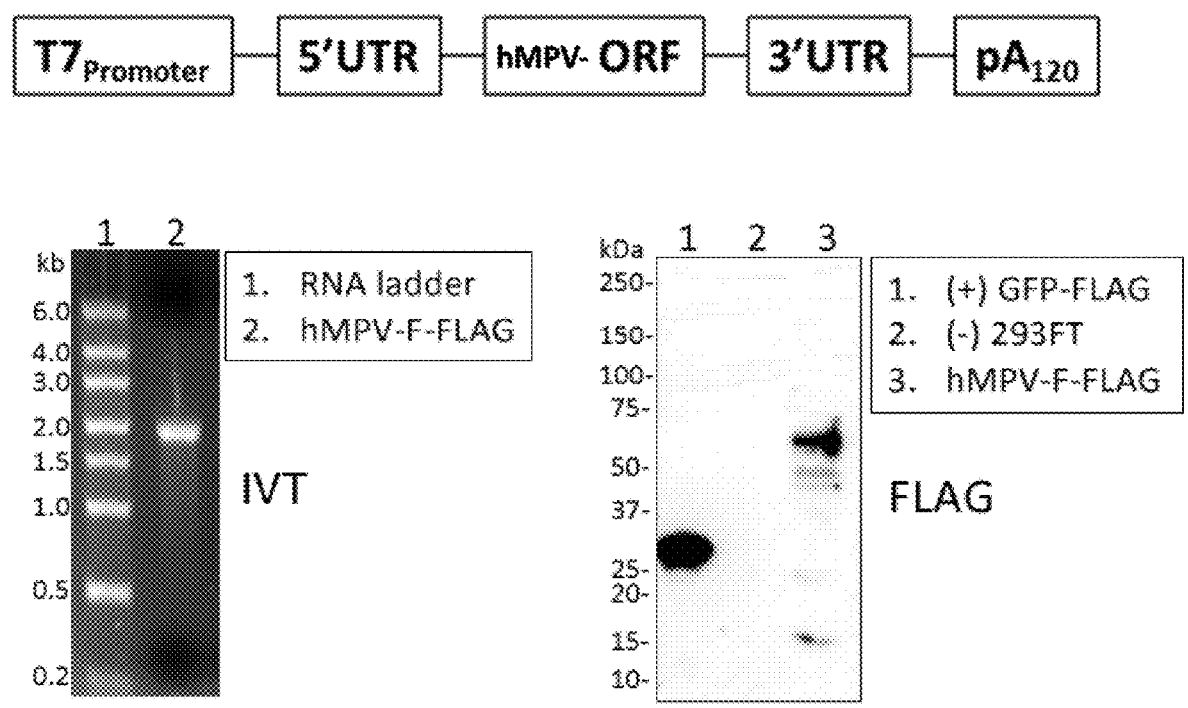
FIG. 8 shows the results of hMPV-F IVT and western blot with FLAG tag.

Example 6—DNA Templates Used for In Vitro Transcription and Protein Expression of hMPV F Genes (See FIG. 8)

DNA constructs used for hPMV F protein mRNA was prepared as shown in FIG. 8 Top.

IVT (FIG. 8 Bottom left): The hMPV F protein mRNA was produced as described at FIG. 8 Bottom Left.

Western blot (FIG. 8 Bottom right): The detection of hMPV F protein from mRNA was conducted as described above for the RSV F proten. Mouse monoclonal anti-FLAG antibody (AB_1957945, Invitrogen) was used for FLAG-tagged hMPV-F protein. The expression of hMPV F protein was detected in the transfected 293 FT cells with mRNA having a FLAG tag at 3' end of hMPV-F ORF as shown in FIG. 8.

Example 7—Immunogenicity Study for RSV Vaccine Composition and hMPV Vaccine Composition This study is designed to test the immunogenicity in mice of the RSV vaccine composition or the RSV and hMPV vaccine composition of the present disclosure.

Mice are immunized intramuscularly (IM) or intradermally (ID) with the RSV vaccine composition of the present disclosure (RSV mutant F B strain, and RSV mutant F A strain) or the RSV and hMPV vaccine composition of the present disclosure (RSV mutant F B strain, RSV mutant F A strain, and hMPV F). The vaccine composition of the present disclosure is chemically modified or unmodified. A total of four immunizations are given at 3-week intervals (i.e., at weeks 0 and 3), and sera are collected after each immunization until weeks 8. Serum antibody titers against RSV mutant F B strain, RSV mutant F A strain, and hMPV F are determined by ELISA. Sera collected from each mouse during weeks 10-16 are, optionally, pooled, and used for virus neutralization assay. Purified IgG antibodies are used for immunoelectron microscopy, antibody-affinity testing, and in vitro protection assays. The spleen in the immunized mice will be harvested and used for T cell responses for various cytokines including TNF alpha, INF-gamma, and IL-2 post peptide stimulation. Doses and formulations will be selected for the virus challenge study.

Example 8—Virus Challenge Study for RSV Vaccine Composition and hMPV Vaccine Composition This study is designed to evaluate the protection efficacy of the RSV vaccine or the RSV and hMPV vaccine against RSV infection and/or hMPV infection in mice post immunization with the proper doses and formulations determined in the Immunogenicity study. The mice will be immunized twice at weeks of 0 and 3, and the immunized mice will be infected by RSV and/or hMPV at week 6. Phenotypes (weight loss, fever, and survival) will be monitored for 2 weeks post infection. Viral titers in sera collected at weeks 1 and 2 post infection will be determined. The sacrificed mice will be examined for pathology.

---

The invention claimed is:

1. A respiratory syncytial virus (RSV) vaccine composition comprising
a messenger ribonucleic acid (mRNA) comprising an open reading frame (ORF) encoding RSV mutant F B strain protein having an amino acid sequence of SEQ ID NO: 1.

2. The RSV vaccine composition according to claim 1, wherein the ORF encoding RSV mutant F B strain protein has a nucleotide sequence of SEQ ID NO: 2.

3. The RSV vaccine composition according to claim 2, wherein the mRNA comprising the ORF encoding RSV mutant F B strain protein further comprises a 5' untranslated region (UTR), a 3' UTR, and a poly (A) tail so as to have the following structure:
5'UTR-ORF encoding RSV mutant F B strain protein-3'UTR-poly (A) tail, and
wherein the ORF encoding RSV mutant F B strain protein has a nucleotide sequence of SEQ ID NO: 2.

4. The RSV vaccine composition according to claim 3, wherein the poly (A) tail has a length of 50-250 nucleotides.

5. The RSV vaccine composition according to claim 3, wherein the mRNA having the structure of 5'UTR-ORF encoding RSV mutant F B strain protein-3'UTR-poly (A) tail has a nucleotide sequence of SEQ ID NO: 3.

6. The RSV vaccine composition according to claim 3, wherein the mRNA having the structure of 5'UTR-ORF encoding RSV mutant F B strain protein-3'UTR-poly (A) tail has a nucleotide sequence having at least 80% identity to SEQ ID NO: 3.

7. The RSV vaccine composition according to claim 1 further comprising a pharmaceutically acceptable carrier.

8. The RSV vaccine composition according to claim 7, wherein the pharmaceutically acceptable carrier is a lipid nanoparticle encapsulating the mRNA therein.

9. A method of inducing immune response against respiratory syncytial virus (RSV) comprising:
administering an effective amount of the RSV vaccine composition according to claim 1 to a subject in need thereof.

10. The RSV vaccine composition according to claim 1 further comprising a mRNA comprising an ORF encoding RSV mutant F A strain protein having an amino acid sequence of SEQ ID NO: 5.

11. The RSV vaccine composition according to claim 10, wherein the ORF encoding RSV mutant F A strain protein has a nucleotide sequence of SEQ ID NO: 6.

12. The RSV vaccine composition according to claim 11, wherein the mRNA comprising the ORF encoding RSV mutant F A strain protein further comprises a 5' untranslated region (UTR), a 3' UTR, and a poly (A) tail so as to have the following structure:
5'UTR-ORF encoding RSV mutant F A strain protein-3'UTR-poly (A) tail, and
wherein the ORF encoding RSV mutant F A strain protein has a nucleotide sequence of SEQ ID NO: 6.

13. The RSV vaccine composition according to claim 12, wherein the poly (A) tail has a length of 50-250 nucleotides.

14. The RSV vaccine composition according to claim 12, wherein the mRNA having the structure of 5'UTR-ORF encoding RSV mutant F A strain protein-3'UTR-poly (A) tail has a nucleotide sequence of SEQ ID NO: 7.

15. The RSV vaccine composition according to claim 12, wherein the mRNA having the structure of 5'UTR-ORF encoding RSV mutant F A strain protein-3'UTR-poly (A) tail has a nucleotide sequence having at least 80% identity to SEQ ID NO: 7.

16. The RSV vaccine composition according to claim 10 further comprising a pharmaceutically acceptable carrier.

17. The RSV vaccine composition according to claim 16, wherein the pharmaceutically acceptable carrier is a lipid nanoparticle encapsulating the mRNA therein.

18. A method of inducing immune response against respiratory syncytial virus (RSV) comprising:
administering an effective amount of the RSV vaccine composition according to claim 10 to a subject in need thereof.

19. A respiratory syncytial virus (RSV) and human metapneumovirus virus (hMPV) vaccine composition comprising
a messenger ribonucleic acid (mRNA) comprising an open reading frame (ORF) encoding RSV mutant F A strain protein having an amino acid sequence of SEQ ID NO: 5,
a mRNA comprising an ORF encoding RSV mutant F B strain protein having an amino acid sequence of SEQ ID NO: 1, and
a mRNA comprising an ORF encoding hMPV F protein having an amino acid sequence of SEQ ID NO: 9.

20. The RSV and hMPV vaccine composition according to claim 19,
wherein the ORF encoding RSV mutant F A strain protein has a nucleotide sequence of SEQ ID NO: 6,
wherein the ORF encoding RSV mutant F B strain protein has a nucleotide sequence of SEQ ID NO: 2, and
wherein the ORF encoding hMPV F protein has a nucleotide sequence of SEQ ID NO: 10.

21. The RSV and hMPV vaccine composition according to claim 20,
(i) wherein the mRNA comprising the ORF encoding RSV mutant F A strain protein further comprises a 5' untranslated region (UTR), a 3' UTR, and a poly (A) tail so as to have the following structure:
5'UTR-ORF encoding RSV mutant F A strain protein-3'UTR-poly (A) tail, and
wherein the ORF encoding RSV mutant F A strain protein has a nucleotide sequence of SEQ ID NO: 6,
(ii) wherein the mRNA comprising the ORF encoding RSV mutant F B strain protein further comprises a 5' untranslated region (UTR), a 3' UTR, and a poly (A) tail so as to have the following structure:
5'UTR-ORF encoding RSV mutant F B strain protein-3'UTR-poly (A) tail, and
wherein the ORF encoding RSV mutant F B strain protein has a nucleotide sequence of SEQ ID NO: 2, and
(iii) wherein the mRNA comprising the ORF encoding hMPV F protein further comprises a 5' untranslated region (UTR), a 3' UTR, and a poly (A) tail so as to have the following structure:

5'UTR-ORF encoding hMPV F protein-3'UTR-poly (A) tail, and wherein the ORF encoding hMPV F protein has a nucleotide sequence of SEQ ID NO: 10.

22. The RSV and hMPV vaccine composition according to claim 21, wherein the poly (A) tail has a length of 50-250 nucleotides.

23. The RSV and hMPV vaccine composition according to claim 21,
   (i) wherein the mRNA having the structure of 5'UTR-ORF encoding RSV mutant F A strain protein-3'UTR-poly (A) tail has a nucleotide sequence of SEQ ID NO: 7,
   (ii) wherein the mRNA having the structure of 5'UTR-ORF encoding RSV mutant F B strain protein-3'UTR-poly (A) tail has a nucleotide sequence of SEQ ID NO: 3, and
   (iii) wherein the mRNA having the structure of 5'UTR-ORF encoding hMPV F protein-3'UTR-poly (A) tail has a nucleotide sequence of SEQ ID NO: 11.

24. The RSV and hMPV vaccine composition according to claim 21,
   (i) wherein the mRNA having the structure of 5'UTR-ORF encoding RSV mutant F A strain protein-3'UTR-poly (A) tail has a nucleotide sequence having at least 80% identity to SEQ ID NO: 7,
   (ii) wherein the mRNA having the structure of 5'UTR-ORF encoding RSV mutant F B strain protein-3'UTR-poly (A) tail has a nucleotide sequence having at least 80% identity to SEQ ID NO: 3, and
   (iii) wherein the mRNA having the structure of 5'UTR-ORF encoding hMPV F protein-3'UTR-poly (A) tail has a nucleotide sequence having at least 80% identity to SEQ ID NO: 11.

25. The RSV and hMPV vaccine composition according to claim 19 further comprising a pharmaceutically acceptable carrier.

26. The RSV and hMPV vaccine composition according to claim 25, wherein the pharmaceutically acceptable carrier is a lipid nanoparticle encapsulating the mRNA therein.

27. A method of inducing immune response against respiratory syncytial virus (RSV) and human metapneumovirus virus (hMPV) comprising:
   administering an effective amount of the RSV and hMPV vaccine composition according to claim 19 to a subject in need thereof.

\* \* \* \* \*

SEQUENCE LISTING

```
Sequence total quantity: 12
SEQ ID NO: 1            moltype = AA  length = 574
FEATURE                 Location/Qualifiers
source                  1..574
                        mol_type = protein
                        organism = synthetic construct
SEQUENCE: 1
MELLIHRSSA IFLTLAINAL YLTSSQNITE EFYQSTCSAV SRGYLSALRT GWYTSVITIE   60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVCKVLHL EGEVNKIKNA LQLTNKAVVS  180
LSNGVSVLTF RVLDLKNYIN NQLLPMLNRQ SCRISNIETV IEFQQKNSRL LEITREFSVN  240
AGVTTPLSTY MLTNSELLSL INDMPITNDQ KKLMSSNVQI VRQQSYSIMC IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                              574

SEQ ID NO: 2            moltype = RNA  length = 1722
```

| FEATURE | Location/Qualifiers |
|---|---|
| source | 1..1722 |
| | mol_type = other RNA |
| | organism = synthetic construct |

SEQUENCE: 2

```
atggaactgc tgatccacag atccagcgct attttcctga cactggccat caatgccctg   60
tacctgacaa gcagccagaa catcacagag gaattctacc agagtacctg tagcgctgtg  120
tctcggggat acctgagcgc cctgcggacc ggttggtaca ccagcgtgat cacaatcgag  180
ctgagtaaca tcaaggagac aaaatgcaat ggcactgaca ccaaggtgaa acttatcaaa  240
caggagctgg ataagtacaa gaatgccgtg acagaactgc agctgctgat gcagaatacc  300
cccgccgtga caacagagc cagacgggaa gcccctcaat acatgaacta cacaatcaac  360
accacaaaga acctgaacgt gtctatctcc aagaagcgca agcggagatt cctgggcttc  420
ctgttgggag tgggctctgc catcgccagc ggcatcgcag tgtgcaaggt gctgcacctg  480
gaaggagaag tgaacaagat caagaatgcc ctgcagctga ccaacaaggc cgtggtctct  540
ctgagcaatg gcgtgagcgt gctgaccttt agagtgctgg acctgaagaa ctacatcaac  600
aaccagctgc tgcctatgct gaacagacag tcttgtagaa tcagcaacat cgaaaccgtg  660
atcgagttcc agcagaagaa ctccaggctg ctggaaatca agagagagtt tagcgtgaac  720
gccggcgtca ccaccccct gagcacctac atgctgacca acagcgagct gctgagcctg  780
attaacgaca tgcctatcac caatgaccag aaaaagctaa tgagcagcaa tgtgcaaatc  840
gtgcggcagc agtcctacag catcatgtgc atcatcaagg aagaggtcct ggcctacgtg  900
gtacaactgc ctatctacgg cgtgatcgac acccccttgtt ggaagctcca taccagccct  960
ctgtgcacaa caaacatcaa agaaggcagc aatatctgcc tgacaagaac agatagaggc 1020
tggtattgtg acaacgctgg ctccgtctcc ttcttccctc aggccgacac ctgcaaggtg 1080
cagagcaacc gcgtgttctg cgataccatg aacagcttaa cactgcccag cgaggtgtct 1140
ctctgtaaca ccgacatctt caactctaaa tacgactgca agatcatgac ctctaagact 1200
gatatcagca gcagcgtgat tacctcccctg ggcgccatc tgtcttgcta cggcaagaca 1260
aagtgcaccg ccagcaacaa gaaccggggc atcatcaaga ccttcagcaa cggctgcgac 1320
tacgtgagca caagggcgt ggacaccgtt agcgtgggca acacactgta ttacgtaaat 1380
aaacttgagg gcaagaatct gtacgtgaag ggcgagccta tcatcaacta ctacgaccca 1440
ctggtgtttc catctgatga gttcgacgcc tccatctccc aggtgaacga gaagatcaac 1500
cagagcctgg cttttatcag aagaagcgat gagctgctgc acaacgtgaa taccggaaaa 1560
agcaccacca acatcatgat caccgccatc attatcgtta tcatcgtggt gctgctgagt 1620
ctgatcgcca ttggactgct gctgtattgc aaagccaaga caccccccgt gaccctgagc 1680
aaggaccagc tgagcggcat caacaacata gctttctcca ag                    1722
```

| SEQ ID NO: 3 | moltype = RNA  length = 2015 |
|---|---|
| FEATURE | Location/Qualifiers |
| source | 1..2015 |
| | mol_type = other RNA |
| | organism = synthetic construct |

SEQUENCE: 3

```
aggccggcac tcttctggtc cccacagact cagagagaac cgccgccac catggaactg   60
ctgatccaca gatccagcgc tattttcctg cactggccca tcaatgccct gtacctgaca  120
agcagccaga acatcacaga ggaattctac cagagtacct gtagcgctgt gtctcgggga  180
tacctgagcg ccctgcggac cggttggtac accagcgtga tcacaatcga gctgagtaac  240
atcaaggaga caaaatgcaa tggcactgac accaaggtga aacttatcaa acaggagctg  300
gataagtaca agaatgccgt gacagaactg cagctgctga tgcagaatac ccccgccgtg  360
acaacagag ccagacggga agcccctcaa tacatgaact acacaatcaa caccacaaag  420
aacctgaacg tgtctatctc caagaagcgc aagcggagat tcctgggctt cctgttggga  480
gtgggctctg ccatcgccag cggcatcgca gtgtgcaagg tgctgcacct ggaaggagaa  540
gtgaacaaga tcaagaatgc cctgcagctg accaacaagg ccgtggtctc tctgagcaat  600
ggcgtgagcg tgctgacctt tagagtgctg gacctgaaga actacatcaa caaccagctg  660
ctgcctatgc tgaacagaca gtcttgtaga atcagcaaca tcgaaaccgt gatcgagttc  720
cagcagaaga actccaggct gctggaaatc aagagagagt ttagcgtgaa cgccggcgtc  780
accaccccc tgagcaccta catgctgacc aacagcgagc ctgattaacga  840
atgcctatca ccaatgacca gaaaaagcta atgagcagca atgtgcaaat cgtgcggcag  900
cagtcctaca gcatcatgtg catcatcaag gaagaggtcc tggcctacgt ggtacaactg  960
cctatctacg gcgtgatcga cacccccttgt tggaagctcc ataccagccc tctgtgcaca 1020
acaaacatca agaaggcag caatatctgc ctgacaagaa cagatagagg ctggtattgt 1080
gacaacgctg gctccgtctc cttcttccct caggccgaca cctgcaaggt gcagagcaac 1140
cgcgtgttct gcgataccat gaacagctta cactgccca gcgaggtgtc tctctgtaac 1200
accgacatct tcaactctaa atacgactgc aagatcatga cctctaagac tgatatcagc 1260
agcagcgtga ttacctccct gggcgccatc gtgtcttgct acggcaagac aaagtgcacc 1320
gccagcaaca gaaccgggg catcatcaag accttcagca acggctgcga ctacgtgagc 1380
acaagggcg tggacaccgt tagcgtgggc aacacactgt attacgtaaa taaacttgag 1440
ggcaagaatc tgtacgtgaa gggcgagcct atcatcaact actacgaccc actggtgttt 1500
ccatctgatg agttcgacgc ctccatctcc caggtgaacg agaagatcaa ccagagcctg 1560
gcttttatca gaagaagcga tgagctgctg cacaacgtga ataccggaaa aagcaccacc 1620
aacatcatga tcaccgccat cattatcgtt atcatcgtgg tgctgctgag tctgatcgcc 1680
attggactgc tgctgtattg caaagccaag aacaccccg tgaccctgag caaggaccag 1740
ctgagcggca tcaacaacat agctttctcc aagtgactcg agtaagctgg agcctcggtg 1800
gccatgcttc ttgccccttg ggcctccccc agcccctcc tcccttcct gcaccgtac 1860
ccccgtggtc tttgaataaa gtctgagtgg gcggcaaaaa aaaaaaaaaa aaaaaaaaa 1920
aaaaaaaaa aaaaaaaaa aaaaaaaaaa aaaaaaaaaa aaaaaaaaaa 1980
aaaaaaaaaa aaaaaaaaaa aaaaa                                      2015
```

| SEQ ID NO: 4 | moltype = DNA  length = 4757 |
|---|---|
| FEATURE | Location/Qualifiers |
| source | 1..4757 |

```
                    mol_type = other DNA
                    organism = synthetic construct
SEQUENCE: 4
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acctcgcgaa  420
tgcatctaga ttctagatta atacgactca ctataaggcc ggcactcttc tggtccccac  480
agactcagag agaacccgcc gccaccatgg aactgctgat ccacagatcc agcgctattt  540
tcctgacact ggccatcaat gccctgtacc tgacaagcag ccagaacatc acagaggaat  600
tctaccagag tacctgtagc gctgtgtctc ggggatacct gagcgccctg cggaccggtt  660
ggtacaccag cgtgatcaca atcgagctga gtaacatcaa ggagacaaaa tgcaatggca  720
ctgacaccaa ggtgaaactt atcaaacagg agctggataa gtacaagaat gccgtgacag  780
aactgcagct gctgatgcag aatacccccg ccgtgaacaa cagagccaga cgggaagccc  840
ctcaatacat gaactacaca atcaacacca caaagaacct gaacgtgtct atctccaaga  900
agcgcaagcg gagattcctg ggcttcctgt gggagtgggg ctctgccatc gccagcggca  960
tcgcagtgtg caaggtgctg cacctggaag gagaagtgaa caagatcaag aatgccctgc 1020
agctgaccaa caaggccgtg gtctctctga gcaatggcgt gagcgtgctg acctttagag 1080
tgctggacct gaagaactac atcaacaacc agctgctgcc tatgctgaac agacagtctt 1140
gtagaatcag caacatcgaa accgtgatcg agttccagca gaagaactcc aggctgctgg 1200
aaatcacaag agagtttagc gtgaacgccg gcgtcaccac cccctgagc acctacatgc 1260
tgaccaacag cgagctgctg agcctgatta cgacatgcc tatcaccaat gaccagaaaa 1320
agctaatgac cagcaatgtg caaatcgtgc ggcagcagtc ctacagcatc atgtgcatca 1380
tcaaggaaga ggtcctggcc tacgtggtac aactgcctat ctacggcgtg atcgacaccc 1440
cttgttggaa gctccatacc agccctctgt gcacaacaaa catcaaagaa ggcagcaata 1500
tctgcctgac aagaacagat agaggctggt attgtgacaa cgctggctcc gtctccttct 1560
tccctcaggc cgacactgc aaggtgcaga gcaaccgcgt gttctgcgat accatgaaca 1620
gcttaacact gcccagcgag gtgtctctct gtaacaccga catcttcaac tctaaatacg 1680
actgcaagat catgaccgtct aagactgata tcagcagcag cgtgattacc tccctgggcg 1740
ccatcgtgtc ttgctacggc aagacaaagt gcaccgccag caacaagaac cggggcatca 1800
tcaagaccttt cagcaacggc tgcgactacg tgagcaacaa gggcgtggac accgttagcg 1860
tgggcaacac actgtattac gtaaaataaac ttgagggcaa gaatctgtac gtgaagggcg 1920
agcctatcat caactactac gacccactgg tgtttccatc tgatgagttc gacgcctcca 1980
tctcccaggt gaacgagaag atcaaccaga gcctggcttt tatcagaaga agcgatgagc 2040
tgctgcacaa cgtgaatacc ggaaaaagca ccaccaacat catgatcacc gccatcatta 2100
tcgtttatcat cgtggtgctg ctgagtctga tcgccattgg actgctgctg tattgcaaag 2160
ccaagaacac ccccgtgacc ctgagcaagg accagctgag cggcatcaac aacatagctt 2220
tctccaagtg actcgagtaa gctggagcct cggtggccat gcttcttgcc ccttgggcct 2280
ccccccagcc cctcctcccc ttcctgcacc cgtaccccg tggtctttga ataaagtctg 2340
agtgggcggc aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa tgaagagcat cggatcccgg gcccgtcgac tgcagaggcc tgcatgcaag 2520
cttggcgtaa tcatggtcat agctgtttcc tgtgtgaaat tgttatccgc tcacaattcc 2580
acacaacata cgagccggaa gcataaagtg taaagcctgg ggtgcctaat gagtgagcta 2640
actcacatta attgcgttgc gctcactgcc cgctttccag tcgggaaacc tgtcgtgcca 2700
gctgcattaa tgaatcggcc aacgcgcggg gagaggcggt ttgcgtattg ggcgctcttc 2760
cgcttcctcg ctcactgact cgctgcgctc ggtcgttcgg ctgcggcgag cggtatcagc 2820
tcactcaaag gcggtaatac ggttatccac agaatcaggg gataacgcag gaaagaacat 2880
gtgagcaaaa ggccagcaaa aggccaggaa ccgtaaaaag gccgcgttgc tggcgttttt 2940
ccataggctc cgcccccctg acgagcatca caaaaatcga cgctcaagtc agaggtggcg 3000
aaacccgaca ggactataaa gataccaggc gtttccccct ggaagctccc tcgtgcgctc 3060
tcctgttccg accctgccgc ttaccggata cctgtccgcc tttctccctt cgggaagcgt 3120
ggcgctttct catagctcac gctgtaggta tctcagttcg gtgtaggtcg ttcgctccaa 3180
gctgggctgt gtgcacgaac cccccgttca gcccgaccgc tgcgccttat ccggtaacta 3240
tcgtcttgag tccaacccgg taagacacga cttatcgcca ctggcagcag ccactggtaa 3300
caggattagc agagcgaggt atgtaggcgg tgctacagag ttcttgaagt ggtggcctaa 3360
ctacggctac actagaagaa cagtatttgg tatctgcgct ctgctgaagc cagttacctt 3420
cggaaaaaga gttggtagct cttgatccgg caaacaaacc accgctggta gcggtggttt 3480
ttttgtttgc aagcagcaga ttacgcgcag aaaaaaagga tctcaagaag atcctttgat 3540
cttttctacg ggtctgacg ctcagtggaa cgaaaactca cgttaaggga ttttggtcat 3600
gagattatca aaaaggatct tcacctagat cctttttaaa taaaatgaa gttttaaatc 3660
aatctaaagt atatatgagt aaacttggtc tgacagttac caatgcttaa tcagtgaggc 3720
acctatctca gcgatctgtc tatttcgttc atccatagtt gcctgactcc ccgtcgtgta 3780
gataactacg atacgggagg gcttaccatc tggccccagt gctgcaatga taccgcgaga 3840
cccacgctca ccggctccag atttatcagc aataaaccag ccagccggaa gggccggagc 3900
cagaagtggt cctgcaactt tatccgcctc catccagtct attaattgtt gccgggaagc 3960
tagagtaagt agttcgccag ttaatagttt cgcaacgttg ttgccattg ctacaggcat 4020
cgtggtgtca cgctcgtcgt ttggtatggc ttcattcagc tccggttccc aacgatcaag 4080
gcgagttaca tgatccccca tgttgtgcaa aaaagcggtt agctccttcg gtcctccgat 4140
cgttgtcaga agtaagttgg ccgcagtgtt atcactcatg gttatggcag cactgcataa 4200
ttctcttact gtcatgccat ccgtaagatg cttttctgtg actggtgagt actcaaccaa 4260
gtcattctga gaatagtgta tgcggcgacc gagttgctct tgcccggcgt caatacggga 4320
taataccgcg ccacatagca gaactttaaa agtgctcatc attggaaaac gttcttcggg 4380
gcgaaaactc tcaaggatct taccgctgtt gagatccagt tcgatgtaac ccactcgtgc 4440
acccaactga tcttcagcat cttttacttt caccagcgtt tctgggtgag caaaaacagg 4500
aaggcaaaat gccgcaaaaa agggaataag ggcgacacgg aaatgttgaa tactcatact 4560
```

```
cttcctttttt caatattatt gaagcattta tcagggttat tgtctcatga gcggatacat    4620
atttgaatgt  atttagaaaa ataaacaaat  aggggttccg cgcacatttc cccgaaaagt    4680
gccacctgac  gtctaagaaa ccattattat catgacatta  acctataaaa ataggcgtat    4740
cacgaggccc  tttcgtc                                                    4757

SEQ ID NO: 5             moltype = AA   length = 574
FEATURE                  Location/Qualifiers
source                   1..574
                         mol_type = protein
                         organism = synthetic construct
SEQUENCE: 5
MELLILKANA ITTILTAVTF CFASGQNITE EFYQSTCSAV SKGYLSALRT GWYTSVITIE    60
LSNIKNKCN  GTDAKVKLIK QELDKYKNAV TELQLLMQST QATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYYVN KQEGKSLYVK GEPIINFYDP    480
LVFPSDEFDA SISQVNEKIN QSLAFIRKSD ELLHNVNAGK STTNIMITTI IIVIIVILLS    540
LIAVGLLLYC KARSTPVTLS KDQLSGINNI AFSN                                574

SEQ ID NO: 6             moltype = RNA  length = 1722
FEATURE                  Location/Qualifiers
source                   1..1722
                         mol_type = other RNA
                         organism = synthetic construct
SEQUENCE: 6
atggaactgc tgatcctgaa ggccaacgct atcacaacca tcctcaccgc cgtgacattc    60
tgcttcgcca gcggccagaa cattaccgaa gagttctacc agagcacctg ctccgctgtg    120
tctaaagggt acctgtccgc cctgagaacc ggctggtata ccagcgtgat tacgattgag    180
ctgagcaaca tcaagaagaa caagtgcaac ggaacagacg ccaaggtgaa gctgatcaag    240
caggagctgg ataagtataa gaacgccgtg accgagttgc agctgctcat gcagtctaca    300
caggccacaa acaatcgggc cagaagagag ctgcctagat tcatgaacta cacctgaac    360
aacgccaaga agacaaatgt gaccctgagc aagaaaagaa agcggagatt cctgggcttc    420
ctgctcggcg ttggctctgc catcgccagc ggagtcgccg tgtgcaaagt gctgcacctg    480
gaaggagaag tgaacaagat caagagcgcc ctgctgtcta cgaacaaagc cgtggtgagc    540
ctgtccaacg gcgtgagcgt gctgaccttc aaggtgctgg acctgaagaa ctacatcgat    600
aagcaactgc tgccaatcct gaacaagcag tcttgtagca tcagcaatat cgagacagtg    660
atcgagttcc agcagaagaa caaccggctg ctgaaatcaa cacggggaatt tagcgtcaac    720
gccggtgtga ccacccctgt gtctacctac atgctgacca atagcgagct gctgagcctg    780
atcaatgaca tgcctattac caacgaccaa agaaactga tgagcaacaa tgtacaaatc    840
gttagacgac agagctactc catcatgtgc atcatcaagg aggaagtgct ggctacgtc    900
gtgcaactgc ctctgtacgg cgtgatcgac acccccttgtt ggaagctgca cacgagccct    960
ctgtgcacaa ctaatacaaa ggaaggcagc aacatctgcc tgaccagaac agatagaggc    1020
tggtactgcg acaacgctgg atctgtcagc ttttttccctc aggctgaaac ctgtaaagtg    1080
cagtccaacc gcgtgttttg cgatacaatg aactctctga cactgcctag cgaggtgaac    1140
ctgtgtaatg tggacatctt caaccccaag tacgattgca gatcatgac aagcaagacc    1200
gatgtgtcta gcagcgtgat taccagcctg ggcgccatcg tgtcatgcta cggcaagacc    1260
aagtgcaccg ccagcaacaa aaatcggggc atcatcaaaa ccttcagcaa cggctgcgac    1320
tacgtgagca acaaaggagt ggacaccgtc tccgtgggca caccctgta ctacgtgaac    1380
aagcaggagg gcaagtctct gtacgtgaag ggcgagccaa tcattaactt ctacgacccc    1440
ctggtgttcc cctctgatga gttcgacgcc tccatcagcc aggtgaacga gaagatcaac    1500
cagagcctgg ccttcatcag aaagagcgac gagctgctgc acaacgtcaa tgccggcaaa    1560
agcaccacca acatcatgat caccaccatc atcatcgtga tcattgtgat cctgctgagt    1620
ctgatcgctg tggggccgct gctgtattgt aaagctaggt ccaccccgt gacacttagc    1680
aaggaccagc tgagcggcat caacaacatc gcatttagca ac                      1722

SEQ ID NO: 7             moltype =     length =
SEQUENCE: 7
000

SEQ ID NO: 8             moltype = DNA  length = 4620
FEATURE                  Location/Qualifiers
source                   1..4620
                         mol_type = other DNA
                         organism = synthetic construct
SEQUENCE: 8
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctggg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aaggggatcg gtgcgggcc tcttcgctat    300
tacgccagct ggcgaaaggg ggatgtgctg caaggcgatt aagttgggta acgccagggt    360
tttcccagtc acgacgttgt aaaacgacgg ccagagaatt cgagctcggt acctcgcgaa    420
tacatctaga ttaatacgac tcactataag gccggcactc ttctggtccc cacagactca    480
gagagaaccc gccgccacca tggaactgct gatcctgaag gccaacgcta tcacaaccat    540
cctcaccgcc gtgacattct gcttcgccag cggccagaac atcaccgaag agttctacca    600
gagcacctgc tccgctgtgt ctaaagggta cctgtccgcc ctgagaaccg gctggtatac    660
```

-continued

```
cagcgtgatt acgattgagc tgagcaacat caagaagaac aagtgcaacg gaacagacgc   720
caaggtgaag ctgatcaagc aggagctgga taagtataag aacgccgtga ccgagttgca   780
gctgctcatg cagtctacac aggccacaaa caatcgggcc agaagagagc tgcctagatt   840
catgaactac accctgaaca acgccaagaa gacaaatgtg accctgagca agaaaagaaa   900
gcggagattc ctgggcttcc tgctcggcgt tggctctgca atcgccagcg gagtcgccat   960
gtgcaaagtg ctgcacctgg aaggagaagt gaacaagatc aagagcgccc tgctgtctac  1020
gaacaaagcc gtggtgagcc tgtccaacgg cgtgagcgtg ctgaccttca aggtgctgga  1080
cctgaagaac tacatcgata gcaactgct gccaatcctg aacaagcagt cttgtagcat  1140
cagcaatatc gagacagtga tcgagttcca gcagaagaac aaccggctgc tggaaatcac  1200
acgggaattt agcgtcaacg ccggtgtgac caccccctgtg tctacctaca tgctgaccaa  1260
tagcgagctg ctgagcctga tcaatgacat gcctattacc aacgaccaaa agaaactgat  1320
gagcaacaat gtacaaatcg ttagacagca gagctactcc atcatgtgca tcatcaagga  1380
ggaagtgctg gcctacgtcg tgcaactgcc tctgtacggc gtgatcgaca cccccttgttg  1440
gaagctgcac acgagccctc tgtgcacaac taatacaagg gaaggcagca acatctgcct  1500
gaccagaaca gatagaggct ggtactgcga caacgctgga tctgtcagct tttttccctca  1560
ggctgaaacc tgtaaagtgc agtccaaccg cgtgttttgc gatacaatga actctctgac  1620
actgcctagc gaggtgaacc tgtgtaatgt ggacatcttc aaccccaagt acgattgcaa  1680
gatcatgaca agcaagaccg atgtgtctag cagcgtgatt accagcctgg gcgccatcgt  1740
gtcatgctac ggcaagacca agtgcaccgc cagcaacaaa atcggggca tcatcaaaac  1800
cttcagcaac ggctgcgact acgtgagcaa caaggagtg gacaccgtct ccgtgggcaa  1860
caccctgtac tacgtgaaca gcaggaggg caagtctctg tacgtgaagg gcgagccaat  1920
cattaacttc tacgaccccc tggtgttccc ctctgatgag ttcgacgcct ccatcagcca  1980
ggtgaacgag aagatcaacc agagcctggc cttcatcaga aagagcgacg agctgctgca  2040
caacgtcaat gccggcaaaa gcaccaccaa catcatgatc accaccatca tcatcgtgat  2100
cattgtgatc ctgctgagtc tgatcgctgt gggcctgctg ctgtattgta aagctaggtc  2160
caccccgtg acacttagca aggaccagct gagcggcatc acaacatcg catttagcaa  2220
ctgataaagc tggagcctcg gtggccttgc ttcttgcccc ttgggcctcc ccccagcccc  2280
tcctcccctt cctgcacccg tacccccgtg gtctttgaat aaagtctgag tgggcggcaa  2340
aaaaaaaaaa aaaaaaaaa aaaaaaaaa aaaaaaaaa aaaaaaaaa aaaaaaaaa  2400
aaaaaaaaaa aaaaaaaaa aaaaaaaaa aaaaaaaaa aaaaaaaagg  2460
gcccgtttaa acatcggatc ccgggcccgt cgactgcaga ggcctgcatg caagcttggt  2520
gtaatcatgg tcatagctgt ttcctgtgtg aaattgttat ccgctcacaa ttccacacaa  2580
catacgagcc ggaagcataa agtgtaaagc ctggggtgcc taatgagtga gctaactcac  2640
attaattgcg ttgcgctcac tgcccgcttt ccagtcggga aacctgtcgt gccagctgca  2700
ttaatgaatc ggccaacgcg cggggagagg cggtttgcgt attgggcgct cttccgcttc  2760
ctcgctcact gactcgctgc gctcggtcgt tcggctgcgg cgagcggtat cagctcactc  2820
aaaggcggta atacggttat ccacagaatc aggggataac gcaggaaaga acatgtgagc  2880
aaaaggccag caaaaggcca ggaaccgtaa aaaggccgcg ttgctggcgt ttttccatag  2940
gctccgcccc cctgacgagc atcacaaaaa tcgacgctca agtcagaggt ggcgaaaccc  3000
gacaggacta taaagatacc aggcgtttcc ccctggaagc tccctcgtgc gctctcctgt  3060
tccgaccctg ccgcttaccg gatacctgtc cgcctttctc ccttcgggaa gcgtggcgct  3120
ttctcatagc tcacgctgta ggtatctcag ttcggtgtag tcgttcgct caagctggg  3180
ctgtgtgcac gaacccccg ttcagcccga ccgctgcgcc ttatccggta actatcgtct  3240
tgagtccaac ccggtaagac acgacttatc gccactggca gcagccactg gtaacaggat  3300
tagcagagcg aggtatgtag gcggtgctac agagttcttg aagtggtggc ctaactacgg  3360
ctacactaga agaacagtat ttggtatctg cgctctgctg aagccagtta ccttcggaaa  3420
aagagttggt agctcttgat ccggcaaaca aaccaccgct ggtagcggtg gtttttttgt  3480
ttgcaagcag cagattacgc gcagaaaaaa aggatctcaa gaagatcctt tgatcttttc  3540
tacggggtct gacgctcagt ggaacgaaaa ctcacgttaa gggattttgg tcatgagatt  3600
atcaaaaagg atcttcacct agatcctttt aaattaaaaa tgaagtttta atcaagccc  3660
aatctgaata atgttacaac caattaacca atttctgatta gaaaaactca tcgagcatca  3720
aatgaaactg caatttattc atatcaggat tatcaatacc atattttga aaagccgtt  3780
tctgtaatga aggagaaaac tcaccgaggc agttccatag gatggcaaga tcctggtatc  3840
ggtctgcgat tccgactcgt ccaacatcaa tacaacctat aatttcccc tcgtcaaaa  3900
taaggttatc aagtgagaaa tcaccatgag tgacgactga atccggtgag aatggcaaaa  3960
gtttatgcat ttcttttccag acttgttcaa caggccagcc attacgctcg tcatcaaaat  4020
cactcgcatc aaccaaaccg ttattcattc gtgattgcgc ctgagcgaga cgaaatacgc  4080
gatcgctgtt aaaaggacaa ttacaaacag gaatcgaatg caaccggcgc aggaacactg  4140
ccagcgcatc aacaatattt tcacctgaat caggatattc ttctaatacc tggaatgctg  4200
ttttccgggg atcgcagtg gtgagtaacc atgcatcatc aggagtacgg ataaaatgct  4260
tgatggtcgg aagaggcata aattccgtca gccagtttag tctgaccatc tcatctgtaa  4320
catcattggc aacgctacct ttgccatgtt tcagaaacaa ctctgcgcca tgggcttcc  4380
catacaagcg atagattgtc gcacctgatt gcccgacatt atcgcgagcc catttatacc  4440
catataaatc agcatccatg ttggaattta atcgcggcct cgacgtttcc cgttgaatat  4500
ggctcataac acccctgtta ttactgttta tgtaagcaga cagttttatt gttcatgatg  4560
atatatttt atcttgtgca atgtaacatc agagattttg agacacgggg cagagctgca  4620
```

```
SEQ ID NO: 9         moltype = AA   length = 539
FEATURE              Location/Qualifiers
source               1..539
                     mol_type = protein
                     organism = synthetic construct
SEQUENCE: 9
MSWKVVIIFS LLITPQHGLK ESYLEESCST ITEGYLSVLR TGWYTNVFTL EVGDVENLTC   60
ADGPSLIKTE LDLTKSALRE LKTVSADQLA REEQIENPRQ SRFVLGAIAL GVATAAAVTA  120
GVAIAKTIRL ESEVTAIKNA LKKTNEAVST LGNGVRVLAT AVRELKDFVS KNLTRAINKN  180
KCDIDDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
```

```
CKVSTGRHPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFENIENS QALVDQSNRI    480
LSSAEKGNTG FIIVIILIAV LGSSMILVSI CIIIKKTKKP TGAPPELSGV TNNGFIPHS     539

SEQ ID NO: 10          moltype = RNA  length = 1617
FEATURE                Location/Qualifiers
source                 1..1617
                       mol_type = other RNA
                       organism = synthetic construct
SEQUENCE: 10
atgagctgga aggtggtgat catcttcagc ctgctgatca cccctcagca cggcctgaaa     60
gagagctacc tggaagaaag ctgctctacc atcacagagg ctacctgag tgtgctgcgg    120
accggctggt acacaaacgt gtttaccctg gaagtgggcg acgtggaaaa cctgacatgc    180
gccgatggcc ccagcctgat taagacagag ctggacctga caaagagcgc cctgagagaa    240
ctgaagacag tcagcgctga tcaactggcc agggaggagc agatcgagaa ccccagacag    300
tccagattcg tgctcggtgc catcgccctg ggcgtggcga cagctgccgc tgttaccgct    360
ggcgtggcta tcgccaagac catcagactg gaatctgagg tgaccgccat caagaatgcc    420
ctgaagaaga ccaatgaggc cgtgtctaca ctgggaaatg gcgtgcgggt gctggctaca    480
gccgtccggg aactgaaaga cttcgtgtcc aagaacttga ccagagccat caacaagaac    540
aagtgcgata tcgacgacct gaagatggcc gtgagcttca gccagttcaa ccggcggttc    600
ctgaacgttg tgcggcagtt tagcgacaac gccggaatca ccccagccat cagcctggac    660
ctgatgaccg acgccgagct ggccagagcc gtgagcaaca tgcctacaag cgccggccag    720
atcaagctga tgctggagaa tcgggccatg gtgagaagaa agggctttgg catcctgatc    780
ggcgtgtacg gcagcagcgt gatctacatg gtgcagctgc ctatcttcgg cgtgatcgat    840
accccttgct ggatcgtgaa ggccgcccct agctgtagcg agaaaaaggg aaactacgcc    900
tgtctgctga gagaagatca gggctggtat tgccagaacc ccggcagcac cgtgtactac    960
cccaacgaga aggactgcga acaagaggc gatcacgtgt ctgcgcacac cgccgccggc    1020
atcaacgttg ctgagcaaag caaggaatgc aacatcaaca tcagccacca caactaccct    1080
tgtaaagtga gcaccggaag acaccccatc tccatggtcg cactctcccc tctgggcgcc    1140
ctggtcgcct gctacaaggg cgtgtcttgt agcatcggaa gcaacgcct tggcatcatc    1200
aagcagctga acaaaggatg ttcttatatc accaaccagg atgccgacac cgtgacaatc    1260
gacaataccg tctaccagct gagcaaggtg gaaggcgagc agcacgtgat taagggcaga    1320
cctgtgtcct ctagcttcga ccccgtgaag ttccccgagg accagttcaa tgtggccctg    1380
gatcaagtgt ttgagaacat cgagaacagc caggccctgg tggaccagag caatagaatc    1440
ctgtcctccg ctgagaaagg caacaccggc ttcatcatcg tgatcatcct gatcgccgtg    1500
ctgggctcta gcatgatcct ggtgtctatc tgcattatta tcaagaaaac caagaagcct    1560
accggcgctc cacctgagct gagcggagtg accaacaacg gcttcatccc tcattct      1617

SEQ ID NO: 11          moltype = RNA  length = 1910
FEATURE                Location/Qualifiers
source                 1..1910
                       mol_type = other RNA
                       organism = synthetic construct
SEQUENCE: 11
aggccggcac tcttctggtc cccacagact cagagagaac ccgccgccac catgagctgg     60
aaggtggtga tcatcttcag cctgctgatc acccctcagc acggcctgaa agagagctac    120
ctggaagaaa gctgctctac catcacagag gctacctgag tgtgctgcg gaccggctgg    180
tacacaaacg tgtttaccct ggaagtgggc gacgtggaaa acctgacatg cgccgatggc    240
cccagcctga ttaagacaga gctggacctg acaaagagcg ccctgagaga actgaagaca    300
gtcagcgctg atcaactggc cagggaggag cagatcgaga accccagaca gtccagattc    360
gtgctcggtg ccatcgccct gggcgtggcg acagctgccg ctgttaccgc tggcgtggta    420
atcgccaaga ccatcagact ggaatctgag gtgaccgcca tcaagaatgc cctgaagaag    480
accaatgagg ccgtgtctac actgggaaat ggcgtgcggg tgctggctac agccgtccgg    540
gaactgaaag acttcgtgtc caagaacttg accagagcca tcaacaagaa caagtgcgat    600
atcgacgacc tgaagatggc cgtgagcttc agccagttca accggcggtt cctgaacgtt    660
gtgcggcagt ttagcgacaa cgccggaatc accccagcca tcagcctgga cctgatgacc    720
gacgccgagc tggccagagc cgtgagcaac atgcctacaa gcgccggcca gatcaagctg    780
atgctggaga atcgggccat ggtgagaaga aagggctttg gcatcctgat cggcgtgtac    840
ggcagcagcg tgatctacat ggtgcagctg cctatcttcg gcgtgatcga taccccttgc    900
tggatcgtga aggccgcccc tagctgtagc gagaaaaagg gaaactacgc ctgtctgctg    960
agagaagatc agggctggta ttgccagaac cccggcagca ccgtgtacta ccccaacgag   1020
aaggactgcg agcaagaggc gatcacgtg tctgcgcaca ccgccgccgg catcaacgtt   1080
gctgagcaaa gcaaggaatg caacatcaac atcagccacca ccaactaccc ttgtaaagtg   1140
agcaccggaa gacaccccat ctccatggtc gcactctccc ctctgggcgc cctgggcgcc   1200
tgctacaagg gcgtgtcttg tagcatcgga agcaacgcg ttggcatcat caagcagctg   1260
aacaaaggat gttcttatat caccaaccag gatgccgaca ccgtgacaat cgacaatacc   1320
gtctaccagc tgagcaaggt ggaaggcgag cagcacgtga ttaagggcag acctgtgtcc   1380
tctagcttcg accccgtgaa gttccccgag gaccagttca atgtggccct ggatcaagtg   1440
tttgagaaca tcgagaacag ccaggccctg gtggaccaga gcaatagaat cctgtcctcc   1500
gctgagaaag gcaacaccgg cttcatcatc gtgatcatcc tgatcgccgt gctgggctct   1560
agcatgatcc tggtgtctat ctgcattatt atcaagaaaa ccaagaagcc taccggcgct   1620
ccacctgagc tgagcggagt gaccaacaac ggcttcatcc ctcattcttg actcgagtaa   1680
gctggagcct cggtggccat gcttcttgcc ccttgggcct ccccccagcc cctcctcccc   1740
ttcctgcacc cgtaccccg tggtctttga ataaagtctg agtgggcggc aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaa              1910

SEQ ID NO: 12          moltype = DNA  length = 4514
FEATURE                Location/Qualifiers
```

```
source              1..4514
                    mol_type = other DNA
                    organism = synthetic construct
SEQUENCE: 12
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttggta acgccagggt    360
tttcccagtc acgacgttgt aaaacgacgg ccagagaatt cgagctcggt acctcgcgaa   420
tacatctaga ttaatacgac tcactataag gccggcactc ttctggtccc cacagactca   480
gagagaaccc gccgccacca tgagctgaa ggtggtgatc atcttcagcc tgctgatcac    540
ccctcagcac ggcctgaaag agagctacct ggaagaagac tgctctacca tcacagagtg   600
ctacctgagt gtgctgcgga ccggctggta cacaaacgtg tttaccctgg aagtgggcga   660
cgtgaaaaac ctgacatgcg ccgatggccc cagcctgatt aagacagagc tggacctgac   720
aaagagcgcc ctgagagaac tgaagacagt cagcgctgat caactggcca gggaggagca   780
gatcgagaac cccagacagt ccagattcgt gctcggtgcc atcgccctgg gcgtggcgac   840
agctgccgct gttaccgctg gcgtggctat cgccaagacc atcagactgg aatctgaggt   900
gaccgccatc aagaatgccc tgaagaagac caatgaggcc gtgtctacac tgggaaatgt   960
cgtgcgggtg ctggctacag ccgtccggga actgaaagac ttcgtgtcca gaacttgac   1020
cagagccatc aacaagaaca agtgcgatat cgacgacctg aagatggccg tgagcttcag  1080
ccagttcaac cggcggttcc tgaacgttgt gcggcagttt agcgacaacg ccggaatcac  1140
cccagccatc agcctggacc tgatgaccga cgccgaactg gccagagcca tcagcaacat  1200
gcctacaagc gccggccaga tcaagctgat gctggagaat cgggccatgg tgagcaacat  1260
gggctttggc atcctgatcg gcgtgtacgg cagcagcgtg atctcatatgg tgcagctgcc  1320
tatcttcggc gtgatcgata cccccttgctg gatcgtgaag gccgcccta gctgtagcga  1380
gaaaaaggga aactacgcct gtctgctgag agaagatcag ggctggtatt gccagaacgc  1440
cggcagcacc gtgtactacc ccaacgagaa ggactgcgaa acaagaggcg atcacgtgtt  1500
ctgcgacacc gccgccggca tcaacgttgc tgagcaaagc aaggaatgca acatcaacat  1560
cagcaccacc aactaccctt gtaaagtgag caccggaaga caccccatct ccatggtcgc  1620
actctcccct ctgggcgccc tggtcgcctc tacaagggc gtgtcttgta gcatcggaag   1680
caaccgcgtt ggcatcatca gcagctgaa caaaggatgt tcttatatca ccaaccagga   1740
tgccgacaac gtgacaatcg acaataccgt taccagctca agcaaggtgg aaggcgagca   1800
gcacgtgatt aagggcagac ctgtgtcctc tagcttcgac cccgtgaagt tccccgagga   1860
ccagttcaat gtggccctgg atcaagtgtt tgagaacatc gagaacagcc aggcctggt   1920
ggaccagagc aatagaatcc tgtcctccgc tgagaaaggc aacaccggct tcatcatcgt   1980
gatcatcctg atcgccgtgc tgggctctag catgatcctg gtgtctatct gcattattat   2040
caagaaaacc aagaagccta ccggcgctcc acctgagctg agcggagtga ccaacaacgg   2100
cttcatccct cattcttgac tcgagtaagc tggagcctcg gtggccatgc ttcttgcccc   2160
ttgggcctcc ccccagcccc tcctccccctt cctgcaccg tacccccgtg gtctttgaat   2220
aaagtctgag tgggcggcaa aaaaaaaaaa aaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa   2340
aaaaaaaaaa aaaaaaatg aagagcatcg gatcccgggc ccgtcgactg cagaggcctg    2400
catgcaagct tggtgtaatc atggtcatag ctgtttcctg tgtgaaattg ttatccgctc   2460
acaattccac acaacatacg agccggaagc ataaagtgta aagcctgggg tgcctaatga   2520
gtgagctaac tcacattaat tgcgttcgc tcactgcccg cttccagtc gggaaacctg    2580
tcgtgccagc tgcattaatg aatcggccaa cgcgcgggga gaggcggttt gcgtattggg   2640
cgctcttccg cttcctcgct cactgactcg ctgcgctcgg tcgttcggct gcggcgagcg   2700
gtatcagctc actcaaaggc ggtaatacgg ttatccacag aatcagggga taacgcagga   2760
aagaacatgt gagcaaaagg ccagcaaaag gccaggaacc gtaaaaaggc cgcgttgctg   2820
gcgtttttcc ataggctccg ccccctgac gagcatcaca aaaatcgacg ctcaagtcag   2880
aggtggcgaa acccgacagg actataaaga taccaggcgt ttccccctgg aagctccctc   2940
gtgcgctctc ctgttccgac cctgccgctt accggatacc tgtccgcctt tctcccttcg   3000
ggaagcgtgg cgctttctca tagctcacgc tgtaggtatc tcagttcggt gtaggtcgtt   3060
cgctccaagc tgggctgtgt gcacgaaccc cccgttcagc ccgaccgctg cgccttatcc   3120
ggtaactatc gtcttgagtc aacccggta agacacgact tatcgccact ggcagcagcc   3180
actggtaaca ggattagcag agcgaggtat gtaggcggtg ctacagagtt cttgaagtgg   3240
tggcctaact acggctacac tagaagaaca gtatttggta tctgcgctct gctgaagcca   3300
gttaccttcg gaaaaagagt tggtagctct tgatccggca aacaaaccac cgctggtagc   3360
ggtggttttt tgtttgcaa gcagcagatt acgcgcagaa aaaaaggatc tcaagaagat   3420
cctttgatct tttctacggg gtctgacgct cagtggaacg aaaactcacg ttaagggatt   3480
ttggtcatga gattatcaaa aaggatcttc acctagatcc ttttaaatta aaaatgaagt   3540
tttaaatcaa gcccaatctg aataatgtta caaccaatta accaattctg attagaaaaa   3600
ctcatcgaga tcaaatgaa actgcaattt attcatatca ggattatcaa taccatattt   3660
ttgaaaaagc cgtttctgta atgaaggaga aaactcaccg aggcagttcc ataggatgcc   3720
aagatcctgg tatcggtctg cgattccgac tcgtccaaca tcaatacaac ctattaattt   3780
ccctcgtca aaataaggt tatcaagtga aaatcacca tgagtgacga ctgaatccgg    3840
tgagaatggc aaaagtttat gcatttcttt ccagacttgt tcaacaggcc agccattacg   3900
ctcgtcatca aaatcactcg catcaaccaa accgttattc attcgtgatt gcgcctgagc   3960
gagacgaaat acgcgatcgc tgttaaaagg acaattacaa acaggaatcg aatgcaaccg   4020
gcgcaggaac actgccagcg catcaacaat attttcacct gaatcaggat attcttctaa   4080
tacctggaat gctgttttc cggggatcgc agtggtgagt aaccatgcat catcaggagt   4140
acggataaaa tgcttgatgg tcggaagagg cataaattcc gtcagccagt ttagtctgac   4200
catctcatct gtaacatcat tggcaacgct acctttgcca tgtttcagaa acaactctgg   4260
cgcatcgggc ttcccataca agcgatagat tgtcgcacct gattgcccga cattatcgcg   4320
```

```
agcccattta tacccatata aatcagcatc catgttggaa tttaatcgcg gcctcgacgt 4380
ttcccgttga atatggctca taacacccct tgtattactg tttatgtaag cagacagttt 4440
tattgttcat gatgatatat ttttatcttg tgcaatgtaa catcagagat tttgagacac 4500
gggccagagc tgca                                                   4514
```